(12) United States Patent
Woodruff

(10) Patent No.: US 12,109,143 B2
(45) Date of Patent: Oct. 8, 2024

(54) BODY SUPPORT WRAP

(71) Applicant: Lauren Elizabeth May Woodruff, Sedalia, CO (US)

(72) Inventor: Lauren Elizabeth May Woodruff, Sedalia, CO (US)

(*) Notice: Subject to any disclaimer, the term of this patent is extended or adjusted under 35 U.S.C. 154(b) by 539 days.

(21) Appl. No.: 17/378,739

(22) Filed: Jul. 18, 2021

(65) Prior Publication Data
US 2021/0338473 A1 Nov. 4, 2021

Related U.S. Application Data

(63) Continuation-in-part of application No. 16/717,053, filed on Dec. 17, 2019, now abandoned.

(60) Provisional application No. 62/780,204, filed on Dec. 15, 2018.

(51) Int. Cl.
*A41D 13/12* (2006.01)
*A41D 13/00* (2006.01)
*A41D 31/18* (2019.01)
*A61F 5/44* (2006.01)

(52) U.S. Cl.
CPC ........ *A61F 5/4408* (2013.01); *A41D 13/0012* (2013.01); *A41D 13/1236* (2013.01); *A41D 31/185* (2019.02)

(58) Field of Classification Search
CPC ............ A41D 13/1236; A41D 13/1245; A41D 13/1281; A41D 31/30; A41D 31/18; A41D 27/20; A41D 2300/332; A41D 2400/70
See application file for complete search history.

(56) References Cited

U.S. PATENT DOCUMENTS

| 5,994,612 A * | 11/1999 | Watkins ................. A41D 31/12 602/41 |
| 8,328,598 B2 * | 12/2012 | Smith ...................... A41C 5/00 450/45 |
| 2015/0237933 A1 * | 8/2015 | Abshire ............. A41D 13/1281 2/114 |

* cited by examiner

Primary Examiner — Sally Haden
(74) Attorney, Agent, or Firm — Roger A. Jackson

(57) ABSTRACT

A body support wrap adapted to encompass a body article of a user while elastically encompassing and supporting a fluid communication element, the body support wrap includes first and second flexible elastomeric surrounding sidewalls that are adjacent to one another and offset on an upper end forming a mouth opening and the first and second sidewalls are evenly displaced on a lower end forming a closed attachment, wherein an interior pocket is formed therebetween the first and second sidewalls that the fluid communication element is disposed through the mouth opening, wherein operationally via the first and second sidewalls elasticity the fluid communication element is held anyplace within the interior pocket in multiple positions adjacent to the user for the convenience and comfort of the user.

13 Claims, 16 Drawing Sheets

BODY SUPPORT WRAP

RELATED APPLICATIONS

This application is a continuation in part of U.S. patent application Ser. No. 16/717,053 filed on Dec. 17, 2019 by Lauren Elizabeth May Woodruff of Sedalia, Colorado, U.S. and William Fletcher Woodruff of Sedalia, Colorado, U.S., wherein this application also claims the benefit of U.S. provisional patent application Ser. No. 62/780,204 filed on Dec. 18, 2018 by Lauren Elizabeth May Woodruff of Sedalia, Colorado, U.S. and William Fletcher Woodruff of Sedalia, Colorado, U.S.

FIELD OF THE INVENTION

The present invention is generally relates to articles of clothing with a specific function or purpose, and more particularly to a flexible removably engageable torso body wrap that can accommodate fluid connections and fluid reservoirs to conveniently hold the fluid connections and fluid reservoirs into place, minimize pain and discomfort, plus also to help to reduce the visibility of the fluid connections and fluid reservoirs.

BACKGROUND OF THE INVENTION

Subsequent to surgery, if needed a patient has a drain(s) positioned therethrough their torso skin and cartilage to a specific cavity within the torso, these drain(s) are typically post-surgery for a time period such that the patient needs to deal with all of the "apparatus" being the tubing and drainage reservoirs, at home, work, school, shopping etc., which can be a real hassle, painful, and unsightly. Also, the medical tubing and fluid reservoirs can include intravenous drug administration post-surgery. The use of surgical drainage absorption or tubing systems and intravenous and catheterized local drug delivery systems are prolific in surgery and post-surgical recovery, with the further requirement that the drain openings and skin stitch areas be kept dry, i.e. only sponge baths would be allowed, additionally, the drains and intravenous drug administration can last for up to four to six weeks before removal of all the drains and intravenous drug administration. For instance, in a standard double mastectomy procedure there is included four drainage ports and boluses (intravenous medicine dose(s)) and an antibiotic bolus with two additional entry points to the body, making for a total of six entry points and tubes as well as five drain and medicine boluses directly at the extremely painful surgical site on the torso.

While there are a handful of garments which are designed to store and carry these devices, being the tubes and reservoirs, they are cumbersome and uncomfortable to wear (utilizing Velcro hook and loop fasteners, sewn seams, and other skin abrasive materials), especially when the wearer or patient spends much of their time in bed as is often the case in surgical recovery. Current designs for mastectomy recovery accessory tops involve material and seams over the breast tissue which must not be compressed to prevent necrosis (cell death) of the surgical site. Pockets or pouches for drains are worn directly below the breasts placing additional weight on the surgical site which impedes healing. The drainage or pump apparatus including bulbs or reservoirs and tubing are then left to swing and move around the patient's surgical site, creating a need for constant management and a risk of pulling or damage during sleep being highly inconvenient and un-comfortable.

Women recovering from mastectomy surgery are often required to wear both drainage tubes, pain management medicine delivery ports, and catheterized antibiotic delivery systems for several weeks after the operation. Drainage apparatus and antibiotic delivery bulbs are stored in three different sites; two pouches attached below the breasts and a fanny pack worn against the skin which creates tangling and discomfort. Numerous other surgical procedures require similar postoperative apparatus associated with the recovery plans prescribed by the surgeons.

It is also often necessary for patients to apply and regularly change bandages and gauze over surgical sites. For example, post-operative breast reconstruction and fat grafting procedures are performed on multiple sites including the torso, lower back, and buttocks, and limbs, which are left open to drain fluids during multiple weeks of recovery. Bandages are wrapped and taped directly to the patient in order to hold the gauze in place. This results in awkward and often ineffective placement as the bandages invariably slide around and often fall off the patients torso skin surface. There is currently no easily viable alternative, which could securely, dynamically and comfortably position the absorbent bandages in place on the torso or other body appendages.

Looking at the prior art in this area starting with U.S. Pat. No. 9,591,880 to Lee et al., that discloses a post-surgical garment that includes a wrap-around material with pouches for comfortable placement for surgical drains, and to keep the drains secure during daily activities, wherein tubing is feed through fixed garment openings or fixed slits with the excess tubing placed in a pouch. In Lee flaps are utilized to cover the openings, see in particular FIG. 2, in a preferred example for Lee, over the shoulder straps are used, see all FIGS. 1, 2, and 3, functioning like bra straps, and the pouches have elastic bands to secure the top of the pouch as the slits or openings for the tubes do not independently secure the tubing to the garment, the openings can have a flap over the top of the opening or slit for protection from water wherein the flap can be attached with a hook and loop fastener. The novelty and non-obviousness in Lee is in the flaps over the openings, self-draining mesh pouches, and a planar body section that wraps about a torso with a closure mechanism.

Further in the applicable prior art in United States Patent Application Publication Number 2015/0237933 to Abshire discloses a device for managing medical tubing that is a bib style child chest cover that includes a pouch all constructed of an elasticized material.

Continuing in the applicable prior art in United States Patent Application Publication Number 2014/0031775 to Criss discloses an undergarment for mastectomy patients in the form of a brassiere that includes a camisole for pressure application to a surgical site also having drainage bulb hangers and slits for tubing.

Next, in looking at the prior art in this area with U.S. Pat. No. 5,158,541 to McCurley again discloses an undergarment for mastectomy patients in the form of a brassiere that includes a camisole that includes compression gauze pads utilizing hook and loop fasteners, noting that no accommodation of tubes or reservoirs is taught in the McCurley undergarment.

Further, in looking at the prior art in this area with U.S. Pat. No. 5,496,205 to Lee, discloses an undergarment in the form of a brassiere that includes hook and loop fastener concealed pockets for different size cups plus valuables, noting that no accommodation of tubes or reservoirs is taught in the Lee '205 undergarment.

Moving onward, in looking at the prior art in this area with U.S. Pat. No. 5,782,670 to Whisman discloses an undergarment for open heart surgery patients in the form of a brassiere that includes a roll of padding to lift the brassiere above and off of the heart surgery incision, noting that no accommodation of tubes or reservoirs is taught in the Whisman undergarment.

Further, in looking at the prior art in this area with U.S. Pat. No. 6,390,885 to Brooks discloses an undergarment for mastectomy patients in the form of a brassiere that includes a camisole that includes breast prosthesis and accommodation of tubes or reservoirs with fixed slits and fixed reservoir pouches with hook and loop fastener tabs.

Next, in the applicable prior art in U.S. Pat. No. 8,733,296 to Douglas et al., discloses a pet abdominal surgical after care garment with leg, chest, and hip attachment loops for securing the garment to the pet, that protects the incision site and limits movement of the pet to enhance healing, although managing medical drain tubing is discussed in the specification there is no teaching as to or accommodation of tubes or reservoirs with slits and reservoir pouches shown in the Figures.

Continuing in the applicable prior art in United States Patent Application Publication Number 2006/0173427 to Urbina discloses a tank-top style undergarment for surgery patients in that includes fixed tubing retainers that have a retainer extension that is removably engageable and fixed reservoir holder pockets.

Further, in the applicable prior art in United States Patent Application Publication Number 2009/0036023 to Bertini discloses a mastectomy bra that has filling cups that can be customized as a prosthetic as the filling cups are selectably filled and sewn closed, there is no teaching as to or accommodation of tubes or reservoirs with slits and reservoir pouches shown in the Figures.

What is needed is a body support wrap that while supporting the tubes and reservoirs, does not utilize cumbersome and uncomfortable to wear fasteners that typically include, fixed hook and loop fasteners, sewn seams, buckles, snaps, and other skin abrasive materials, especially when the wearer or patient spends much of their time in bed as is often the case in surgical recovery. Current designs for mastectomy recovery accessory tops involve material and seams over the breast tissue which must not be compressed to prevent necrosis (cell death) of the surgical site. Fixed in position pockets or pouches for drains are typically worn directly below the breasts placing additional weight on the surgical site which impedes healing. The drainage or pump apparatus including bulbs or reservoirs and tubing are then left to swing and move around the patient's surgical site, creating a need for constant management and a risk of pulling or damage during sleep being highly inconvenient and un-comfortable. Thus the more ideal solution for the present invention of the body support wrap would not have any of the aforementioned bulky fasteners, having a more smooth flexible fabric body cover while at the same time providing support for the tubes and reservoirs and allowing for a wide flexibility in position of the tubes and reservoirs— with no fixed hard openings or fixed pouch edges—as the tubes and reservoirs are differently positioned on every patient, as opposed to many of the above mentioned prior art that has fixed opening and pouches for tubes and reservoirs respectively that allow little leeway in tubes and reservoir position plus having the disadvantage of the opening of pouch having a hard edge that could pull against the tubing of reservoir further causing patient discomfort when the support garment shifts as against the skin say for instance during sleep.

The simplicity of the present invention helps to obliviate the need for such elements as, hook and loop fasteners, sewn seams, buckles, snaps, and the like, wherein the elimination of such elements and improves both the ease of use and comfort of the garment as well. The prior art focuses on the apparatus, monitoring, or stabilizing system being affixed to the body, as opposed to the garment itself. The value and uniqueness of present invention is intrinsic to the simple combination of basic materials (e.g., elastic fabrics and thread) and their unique configuration and construction to create a pouch system which can be used to secure post-surgical medical apparatus to the body. While designed for mastectomy recovery, the present invention may be applied to other post-surgical recoveries in myriad applications beyond what is specifically stated herein.

SUMMARY OF INVENTION

Broadly, the present invention is a body support wrap adapted to encompass a body article of a user while elastically encompassing and supporting a fluid communication element, the body support wrap includes a first flexible elastomeric surrounding sidewall that is about a longitudinal axis, the first flexible elastomeric surrounding sidewall having a first primary end portion and an opposing first secondary end portion with the longitudinal axis spanning therebetween, having a first distance as between the first primary end portion and the first secondary end portion, the first flexible elastomeric surrounding sidewall further including a first inner surface and an opposing first outer surface.

Further included in the body support wrap is a second flexible elastomeric partial surrounding sidewall that is partially about a longwise axis, the second flexible elastomeric surrounding sidewall having a second primary end portion and an opposing second secondary end portion with the longwise axis spanning therebetween, having a second distance as between the second primary end portion and the second secondary end portion, the second flexible elastomeric surrounding sidewall further including a second inner surface and an opposing second outer surface. Additionally, the second flexible elastomeric partial surrounding sidewall includes a lengthwise axis that is perpendicularly positioned to the longwise axis, further the second flexible elastomeric partial surrounding sidewall includes a second principal margin and an opposing second subordinate margin with the lengthwise axis spanning therebetween, wherein the second inner surface is positioned adjacent to a portion of the first outer surface to position the longitudinal axis and said longwise axis to be co-incident to one another.

Also included in the body support wrap is a first means for attachment of the second principal margin to an initial linear section that is disposed on the first outer surface and the initial linear section is positioned in-between the first primary end portion and the first secondary end portion and a second means for attachment of the second subordinate margin to a subsequent linear section disposed on said first outer surface and the subsequent linear section is positioned in-between the first primary end portion and the first secondary end portion, further a lesser third distance is formed as between the initial linear section and the subsequent linear section along the first outer surface and a greater fourth distance is formed as between the initial linear section and the subsequent linear section along the first outer surface due to the first flexible elastomeric surrounding sidewall being about the longitudinal axis resulting in the third and fourth distances as between the initial linear section and the subsequent linear section along the first outer surface.

The body support wrap also has a third means for attachment of the first primary end portion and the first primary end portion along the fourth distance, wherein a mouth is formed as between the first secondary end portion and the second secondary end portion along the fourth distance being from the initial linear section to the subsequent linear section, further an open interior is formed as between the first flexible elastomeric surrounding sidewall first outer surface and the second flexible elastomeric partial surrounding sidewall second inner surface plus as between the first, second, and third means for attachment, wherein operationally the fluid communication element is passed therethrough the mouth and stored in the open interior with the first flexible elastomeric surrounding sidewall encompassing the body article to ultimately hold the fluid communication element is a selected position as against the body article.

These and other objects of the present invention will become more readily appreciated and understood from a consideration of the following detailed description of the exemplary embodiments of the present invention when taken together with the accompanying drawings, in which;

BRIEF DESCRIPTION OF DRAWINGS

FIG. 2 shows a reverse upper perspective view of the body support wrap in relation to FIG. 1, wherein FIG. 2 shows the mouth as between the first and second flexible elastomeric surrounding sidewalls wherein the mouth terminates at the fully shown initial and subsequent linear sections, wherein the mouth leads to the open interior, further the offset opening of the mouth along is shown with the initial and subsequent linear sections being fully shown as opposed to being partially shown in FIG. 1, in addition the third and fourth distances are shown in their relation to one another that is only partially shown in FIG. 1;

FIG. 5 shows cross section cut 5-5 from FIG. 2, wherein FIG. 5 shows in detail the adjacent manner and position of the first and second flexible elastomeric surrounding sidewalls in conjunction with the mouth plus the first and second primary end portions with the third means for attachment and the offset at the opening mouth being adjacent to one another at the first and second secondary end portions, in addition to the first and second distances shown, of the first and second flexible elastomeric surrounding sidewalls, plus the omnidirectional stretch elasticity of the first and second flexible elastomeric surrounding sidewalls;

FIG. 6 shows cross section cut 6-6 from FIG. 2, wherein FIG. 6 shows in detail the adjacent manner and position of the first and second flexible elastomeric surrounding sidewalls in conjunction with the mouth plus the first and second primary end portions with the third means for attachment and the offset at the opening mouth being adjacent to one another at the first and second secondary end portions, in addition to the first distance is shown, plus the positioning in-between of the initial linear section to the first primary end portion and the first secondary end portion;

FIG. 7 shows cross section cut 7-7 from FIG. 2, wherein FIG. 7 shows in detail the adjacent manner and position of the first and second flexible elastomeric surrounding sidewalls in conjunction with the mouth plus the first and second primary end portions with the third means for attachment and the offset at the opening mouth being adjacent to one another at the first and second secondary end portions, in addition to the first distance is shown, plus the positioning in-between of the subsequent linear section to the first primary end portion and the first secondary end portion;

FIG. 9 shows a reverse side elevation view of FIG. 8, wherein FIG. 9 shows a use view of the body support wrap disposed on and elastically encompassing the user body article being the user's torso, wherein shown is the first and second flexible elastomeric surrounding sidewalls in conjunction with the mouth plus the first and second primary end portions with the third means for attachment and the offset at the opening mouth being adjacent to one another at the first and second secondary end portions, in addition the initial and subsequent linear sections are shown with the second distance is shown along with the fifth distance being the offset leading to the open interior along the mouth;

FIG. 14 shows cross section cut 14-14 from FIG. 15, wherein FIG. 14 shows in cross sectional detail the adjacent manner and position of the first and second flexible elastomeric surrounding sidewalls in conjunction with the mouth plus the first and second primary end portions with the third means for attachment and the offset at the opening mouth being adjacent to one another at the first and second secondary end portions, in addition to the first and second distances are shown of the first and second flexible elastomeric surrounding sidewalls, plus the interior pocket elastically encompassing the fluid communication element via both the first and second flexible elastomeric surrounding sidewalls to hold the fluid communication element in any user desired selected position both along the second distance (vertically) and anywhere along the fourth distance (circumferentially about the longitudinal axis, see FIGS. 2, 3, and 4) for a higher degree of user convenience and comfort;

REFERENCE NUMBERS IN DRAWINGS

Figure 1:
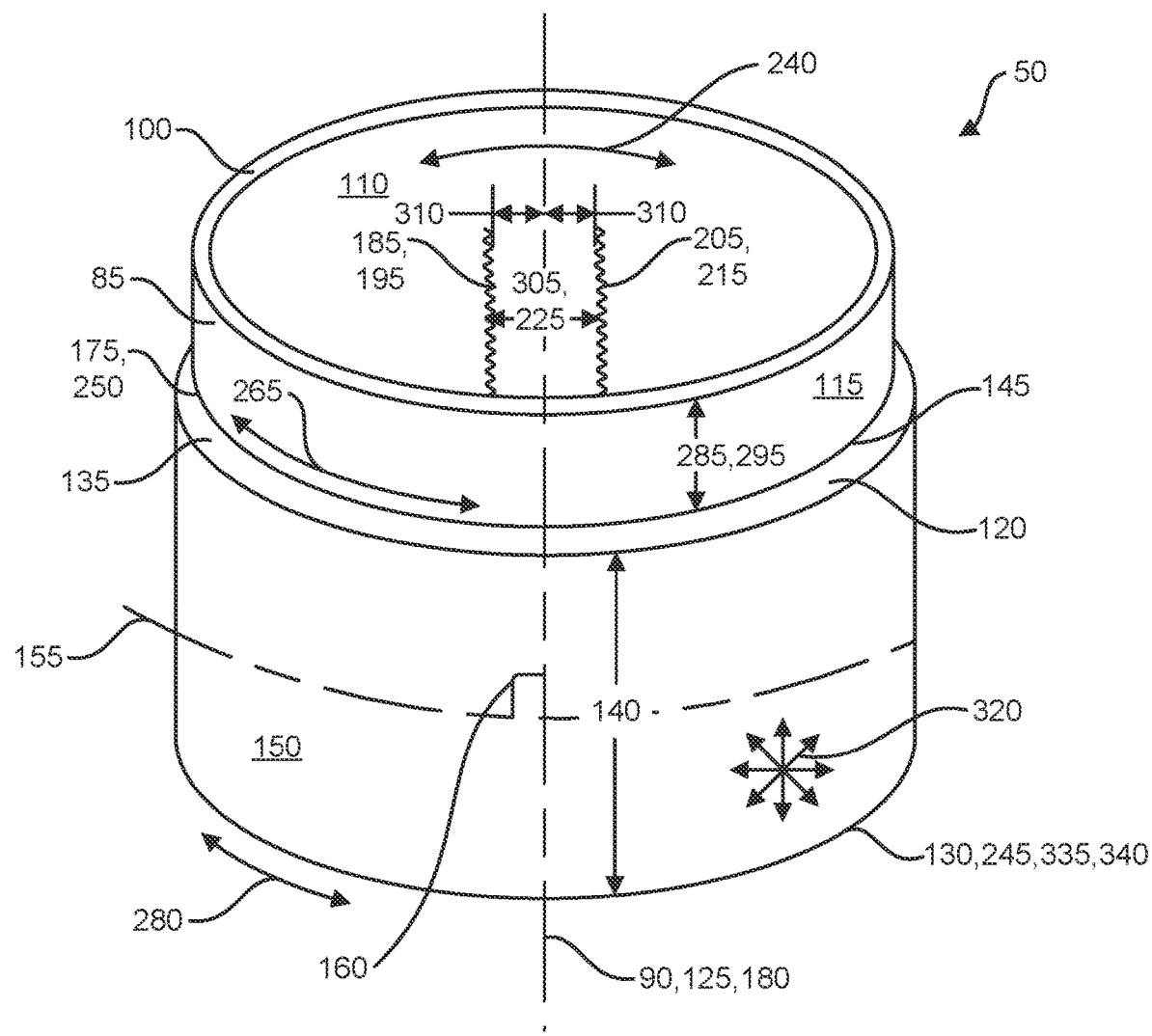
FIG. 1 shows an upper perspective view of the body support wrap that includes the omnidirectional stretch elasticity, the mouth as between the first and second flexible elastomeric surrounding sidewalls, wherein the mouth leads to the open interior, further the offset opening of the mouth along with the initial and subsequent linear sections being shown, in addition the third and fourth distances are shown in their relation to one another that is only partially shown.

50 Body support wrap
55 User
56 Bra of the user 55
60 Body article of the user 55 which can be a leg, arm, torso, neck, or any equivalent
65 Encompassing elastically the body article 60 and the fluid communication element 70 by the
body support wrap 50 or more specifically encompassing the body article 60 and the fluid
communication element 70 by the first 85 and second 120 flexible elastomeric or fabric panel
surrounding sidewalls
70 Fluid communication element
75 Reservoir of the fluid communication element 70
80 Tubing of the fluid communication element 70
85 First flexible elastomeric or fabric panel surrounding sidewall
90 Longitudinal axis
95 First primary end portion of the first flexible elastomeric or fabric panel surrounding sidewall
100 First secondary end portion of the first flexible elastomeric or fabric panel surrounding sidewall 85
105 First distance between the first primary end portion 95 and the first secondary end portion 100

110 First inner surface of the first flexible elastomeric or fabric panel surrounding sidewall 85
115 First outer surface of the first flexible elastomeric or fabric panel surrounding sidewall 85
120 Second flexible elastomeric or fabric panel surrounding sidewall
125 Longwise axis
130 Second primary end portion of the second flexible elastomeric or fabric panel surrounding sidewall 120
135 Second secondary end portion of the second flexible elastomeric or fabric panel surrounding sidewall 120
140 Second distance between the second primary end portion 130 and the second secondary end portion 135
145 Second inner surface of the second flexible elastomeric or fabric panel surrounding sidewall 120
150 Second outer surface of the second flexible elastomeric or fabric panel surrounding sidewall 120
155 Lengthwise axis
160 Perpendicular position of the lengthwise axis 155 and the longwise axis 125
165 Second principal margin of the second flexible elastomeric or fabric panel surrounding sidewall 120
170 Second subordinate margin of the second flexible elastomeric or fabric panel surrounding sidewall 120
175 Adjacent position of the second inner surface 145 to a portion of the first outer surface 115
180 Co-incident position of the longitudinal axis 90 and the longwise axis 125 to one another
185 Initial linear section
190 Disposing of the initial linear section 185 on the first outer surface 115
195 First means for attachment of the second principal margin 165 to the initial linear section 185
200 Positioning in-between of the initial linear section 185 to the first primary end portion 95 and the first secondary end portion 100
205 Subsequent linear section
210 Disposing of the subsequent linear section 205 on the first outer surface 115
215 Second means for attachment of the second subordinate margin 170 to the subsequent linear section 205
220 Positioning in-between of the subsequent linear section 205 to the first primary end portion 95 and the first secondary end portion 100
225 Third distance that is formed as between the initial linear section 185 and the subsequent linear section 205 along the first outer surface 115
230 Fourth distance that is formed as between the initial linear section 185 and the subsequent linear section 205 along the first outer surface 115
235 Fourth distance greater that the third distance 225
240 The first flexible elastomeric or fabric panel surrounding sidewall 85 being about the longitudinal axis 90
245 Third means for attachment of the second primary end portion 130 and the first primary end portion 95 along the fourth distance 230
250 Mouth that is formed as between the first secondary end portion 100 and the second secondary end portion 135 along the fourth distance 230 being from the initial linear section 185 to the subsequent linear section 205
255 Interior pocket that is formed as between the first flexible elastomeric or fabric panel surrounding sidewall 85 first outer surface 115 and the second flexible elastomeric or fabric panel partial surrounding sidewall 120 second inner surface 145 plus as between the first 195, second 215, and third 245 means for attachment
260 Perimeter of the second secondary end portion 135
265 Open interior 255 as defined by extending for the perimeter 260 of the second secondary end portion 135 along the fourth distance 230
270 The fluid communication element 70 being passed therethrough the mouth 250
275 Storing in the interior 255 with the first flexible elastomeric or fabric panel surrounding sidewall 85 encompassing the body article 60 to ultimately hold the fluid communication element 70 in a selected position as against the body article 60
280 Juxtapose structural position of the second primary end portion 130 to the first primary end portion 95
285 Offset opening of the mouth 250
290 Sliding down movement of the fluid communication element 70 down the first outer surface 115 therethrough the mouth 250 proceeding into the interior 255
295 Fifth differential distance
300 Volumetric size of the interior 255
305 Parallel position of the initial linear section 185 to the subsequent linear section 205
310 Parallel position to the longitudinal axis 90 of the initial linear section 185 and the subsequent linear section 205
315 Manual movement that is parallel to the longitudinal axis 90 for ease of disposing the fluid communication element 70 into the interior 255
320 Omni-directional stretch of the first 85 and second 120 flexible elastomeric or fabric panel surrounding sidewalls along the longitudinal 90, longwise 125, and lengthwise 155 axes
325 First surface flush stretch stitching for attachment of the second principal margin 165 to the initial linear section 185
330 Second surface flush stretch stitching for attachment of the second subordinate margin 170 to the subsequent linear section 205
335 Third surface flush stretch stitching for attachment of the second primary end portion 130 and the first primary end portion 95 along the fourth distance 230
340 Minimal protruding ridge from the first 325, second 330, or third 335 surface flush stretch stitching

DETAILED DESCRIPTION

With initial reference to FIG. 1 shown is an upper perspective view of the body support wrap 50 that includes the omnidirectional stretch elasticity 320, the mouth 250 as between the first 85 and second 120 flexible elastomeric surrounding sidewalls, wherein the mouth 250 leads to the open interior 255, further the offset 285 opening of the mouth 250 along with the initial 185 and subsequent 205 linear sections being shown, in addition the third 225 and fourth 230 distances are shown in their relation to one another that is only partially shown.

Figure 2:
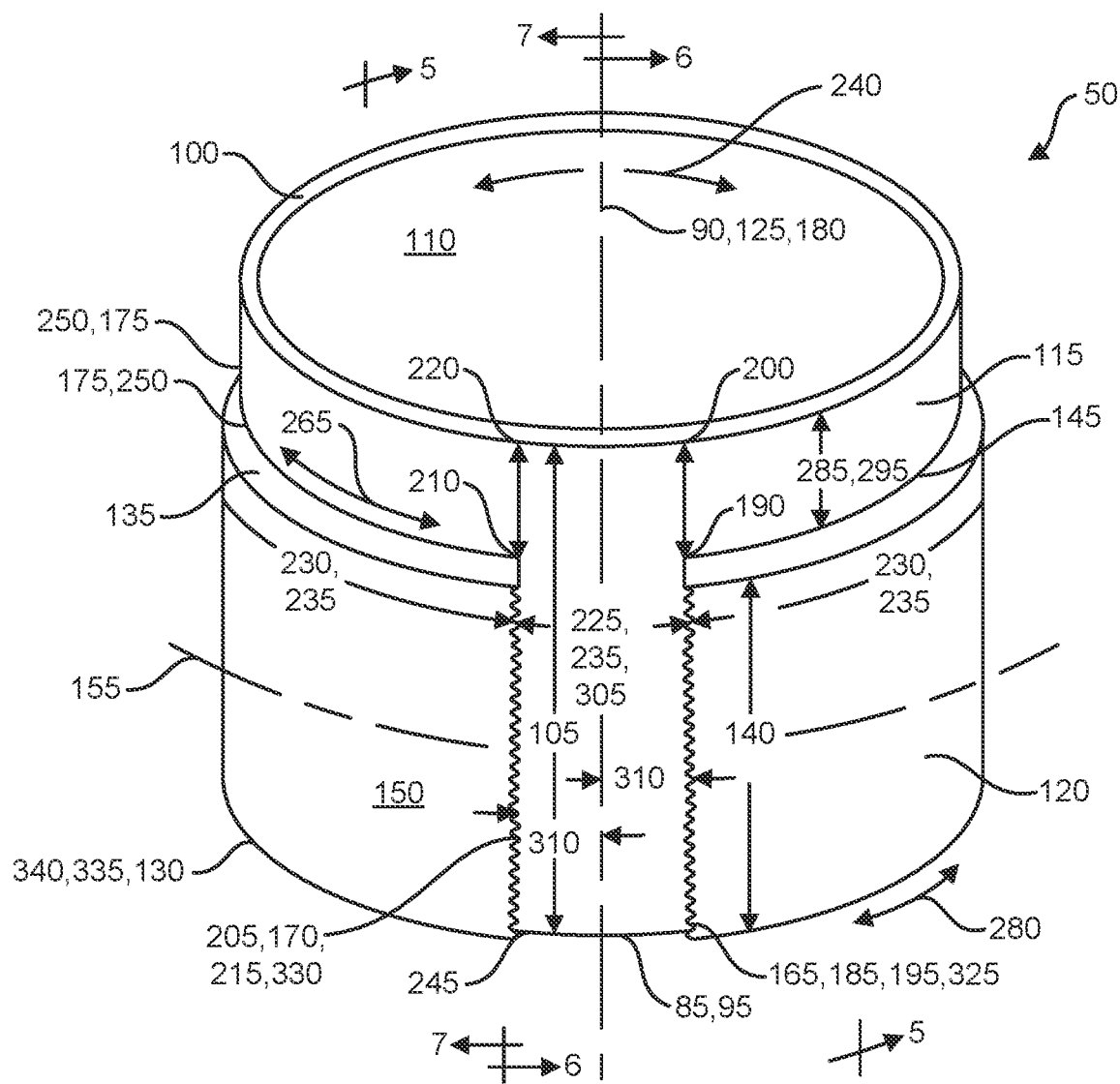

Next, FIG. 2 shows a reverse upper perspective view of the body support wrap 50 in relation to FIG. 1, wherein FIG. 2 shows the mouth 250 as between the first 85 and second 120 flexible elastomeric surrounding sidewalls wherein the mouth 250 terminates at the fully shown initial 185 and subsequent 205 linear sections, wherein the mouth 250 leads to the open 265 interior 255, further the offset 285 opening of the mouth 250 along is shown with the initial 185 and subsequent 205 linear sections being fully shown as opposed to being partially shown in FIG. 1, in addition the third 225 and fourth 230 distances are shown in their relation to one another that is only partially shown in FIG. 1.

Figure 3:
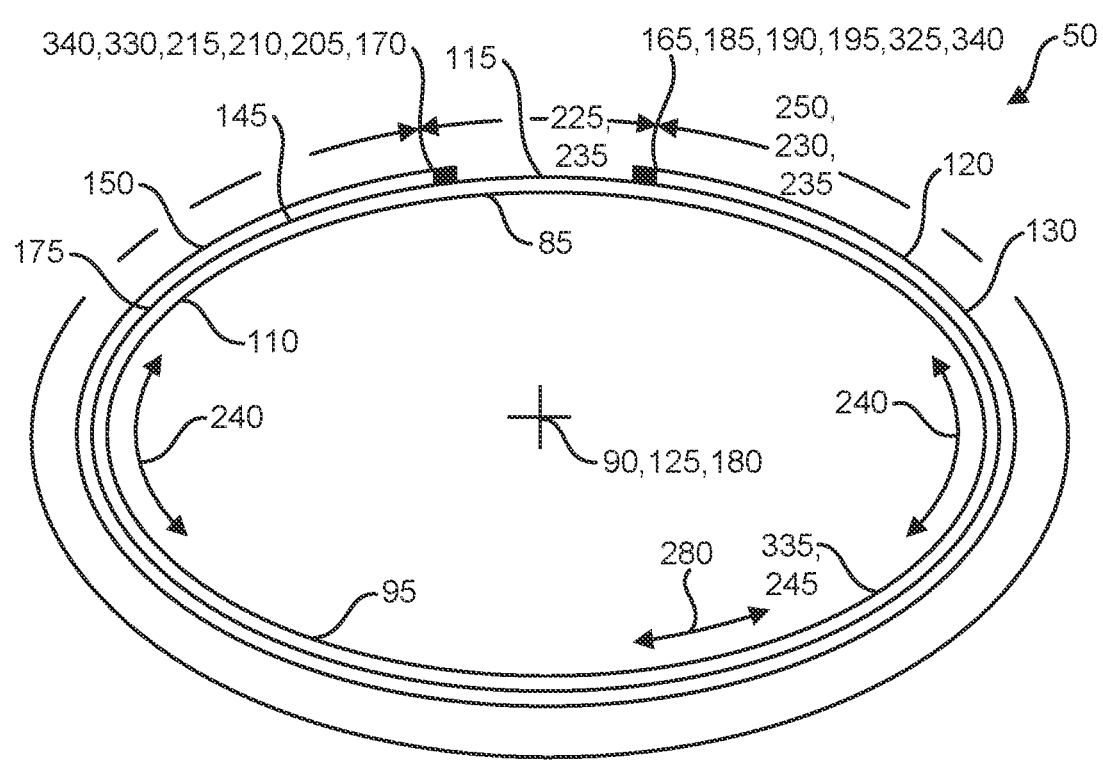
FIG. 3 shows a bottom view of the body support wrap that shows the first and second flexible elastomeric surrounding sidewalls that are adjacent to one another at the first and second primary end portions with the third means for attachment as between the first and second primary end portions, further the initial and subsequent linear sections bottom view is shown that clearly shows the bottom view of the third and fourth distances that are shown in their relation to one another.

Continuing, FIG. 3 shows a bottom view of the body support wrap 50 that shows the first 85 and second 120 flexible elastomeric surrounding sidewalls that are adjacent to one another at the first 95 and second 130 primary end portions with the third means 245 for attachment as between the first 95 and second 130 primary end portions, further the initial 185 and subsequent 205 linear sections bottom view is shown that clearly shows the bottom view of the third 225 and fourth 230 distances that are shown in their relation to one another.

Figure 4:
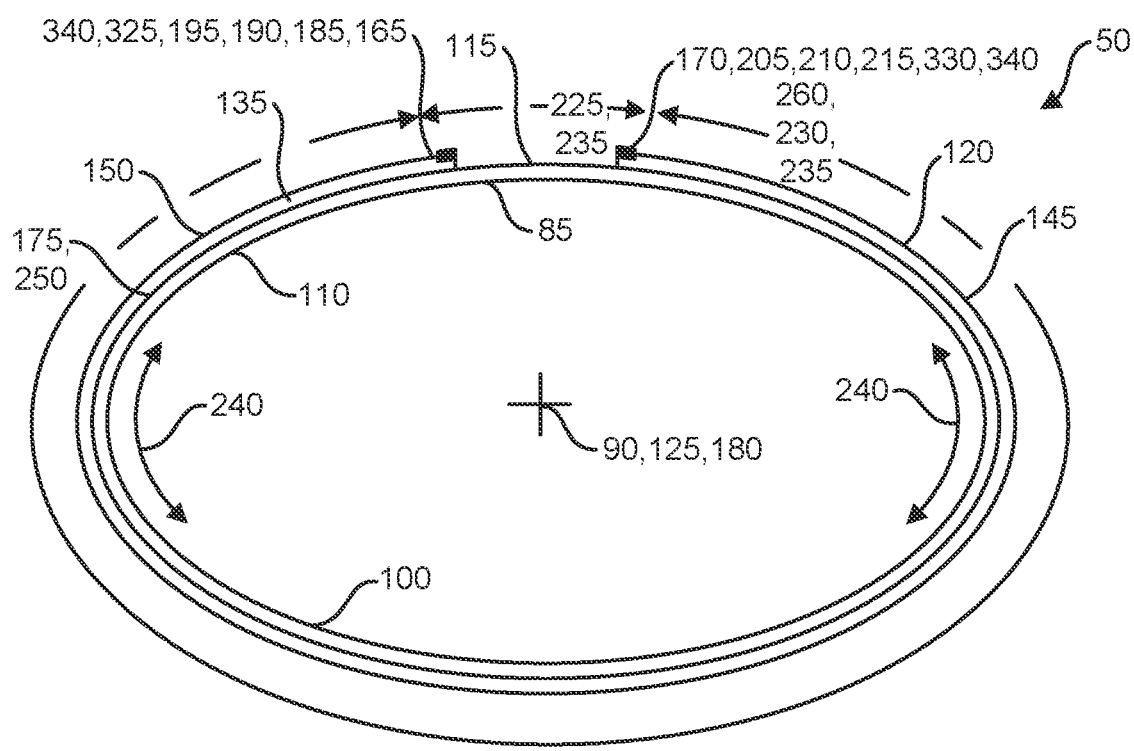
FIG. 4 shows a top view of the body support wrap that shows the first and second flexible elastomeric surrounding sidewalls that are offset at the opening mouth being adjacent to one another at the first and second secondary end portions, further the initial and subsequent linear sections top view is shown that clearly shows the top view of the third and fourth distances that are shown in their relation to one another.

Further, FIG. 4 shows a top view of the body support wrap 50 that shows the first 85 and second 120 flexible elastomeric surrounding sidewalls that are offset 285 at the opening mouth 250 being adjacent to one another at the first 100 and second 135 secondary end portions, further the initial 185 and subsequent 205 linear sections top view is shown that clearly shows the top view of the third 225 and fourth 230 distances that are shown in their relation to one another.

Figure 5:
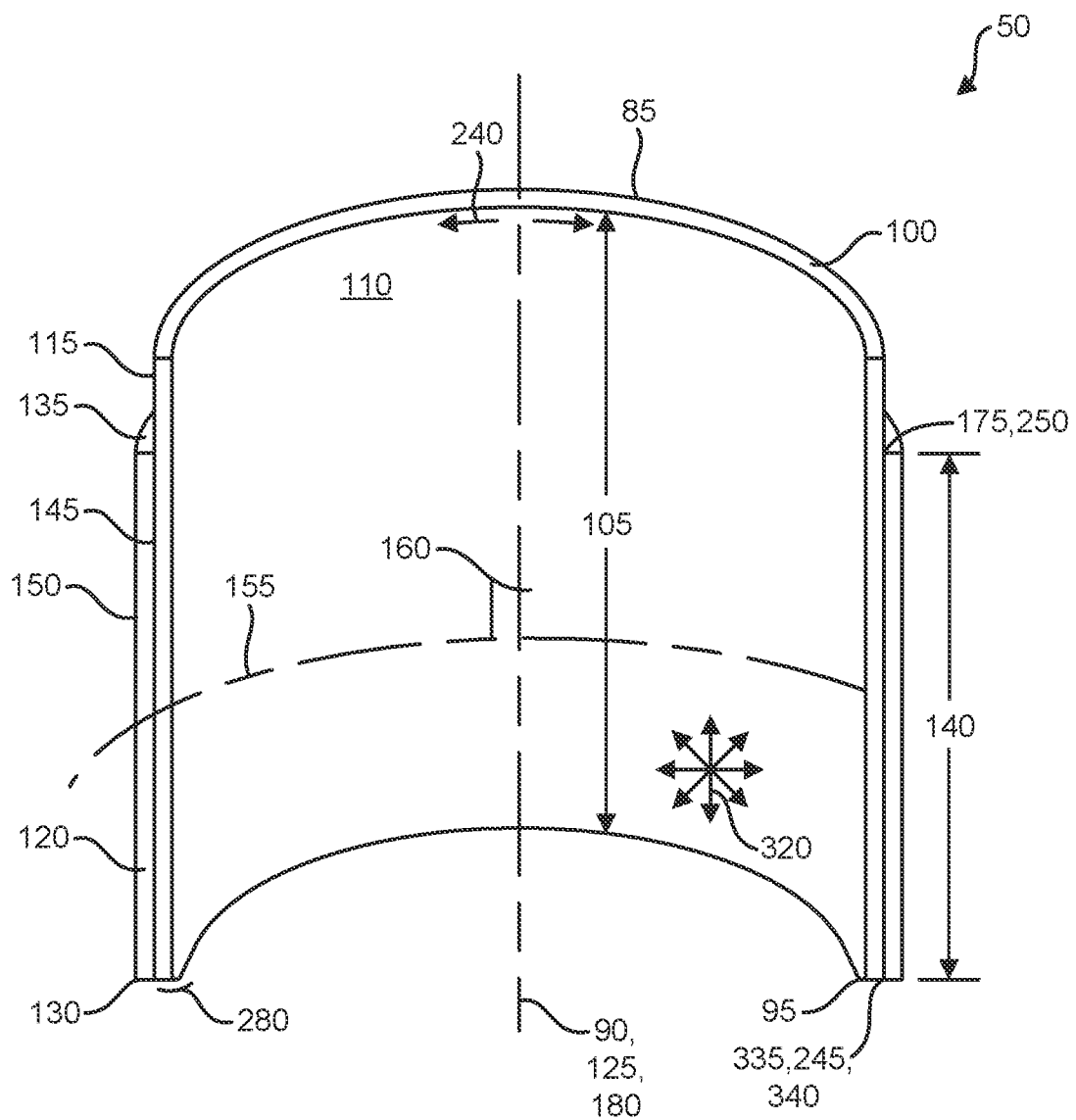

Next, FIG. 5 shows cross section cut 5-5 from FIG. 2, wherein FIG. 5 shows in detail the adjacent manner and position of the first 85 and second 120 flexible elastomeric surrounding sidewalls in conjunction with the mouth 250 plus the first 95 and second 130 primary end portions with the third means 245 for attachment and the offset 285 at the opening mouth 250 being adjacent to one another at the first 100 and second 135 secondary end portions, in addition to the first 105 and second 140 distances shown, of the first 85 and second 120 flexible elastomeric surrounding sidewalls, plus the omnidirectional stretch elasticity 320 of the first 85 and second 120 flexible elastomeric surrounding sidewalls.

Figure 6:
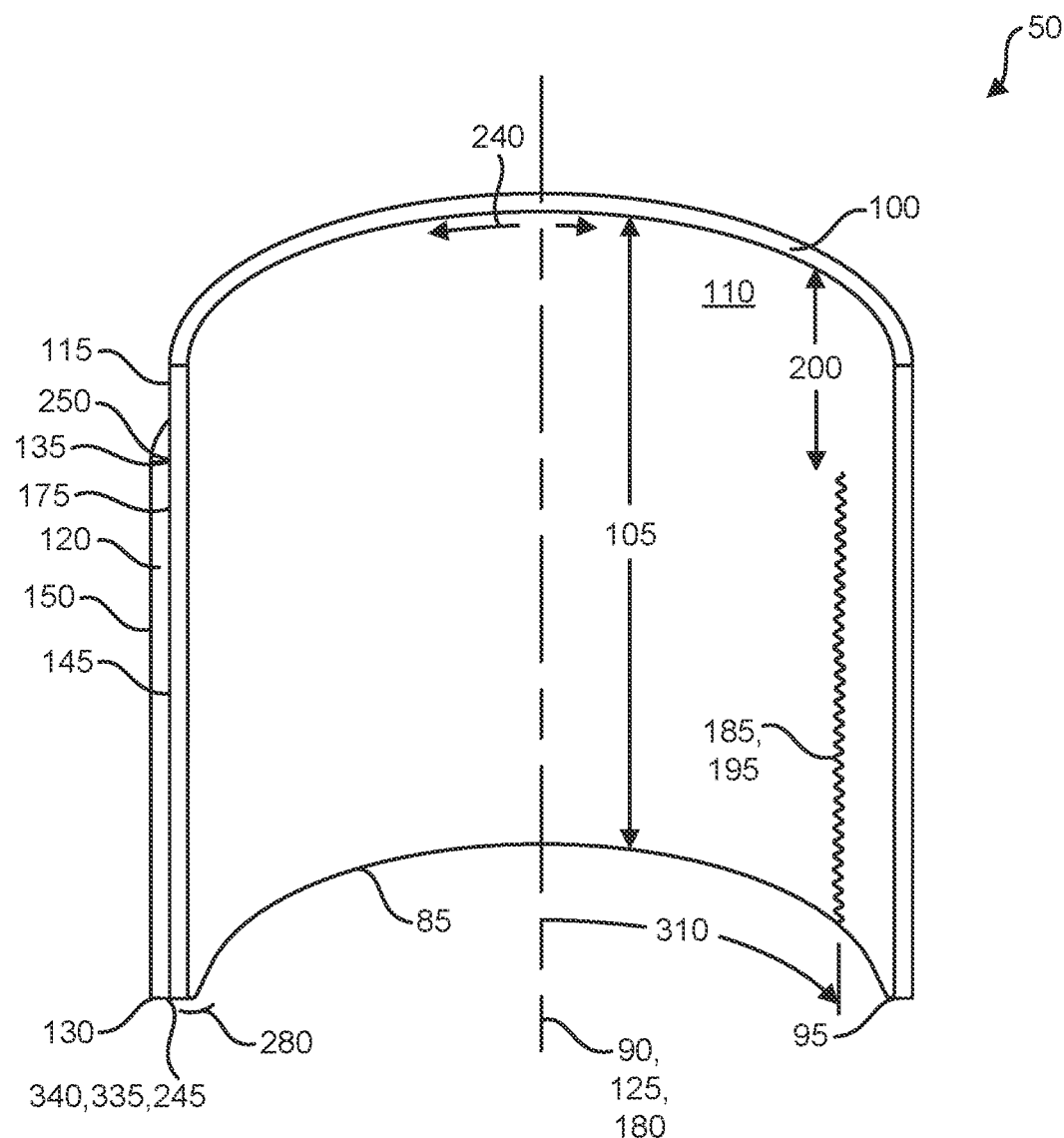

Moving onward, FIG. 6 shows cross section cut 6-6 from FIG. 2, wherein FIG. 6 shows in detail the adjacent manner and position of the first 85 and second 120 flexible elastomeric surrounding sidewalls in conjunction with the mouth 250 plus the first 95 and second 130 primary end portions with the third means 245 for attachment and the offset 285 at the opening mouth 250 being adjacent 175 to one another at the first 100 and second 135 secondary end portions, in addition to the first distance 105 is shown, plus the positioning in-between of the initial linear section 185 to the first primary end portion 95 and the first secondary end portion 100.

Figure 7:
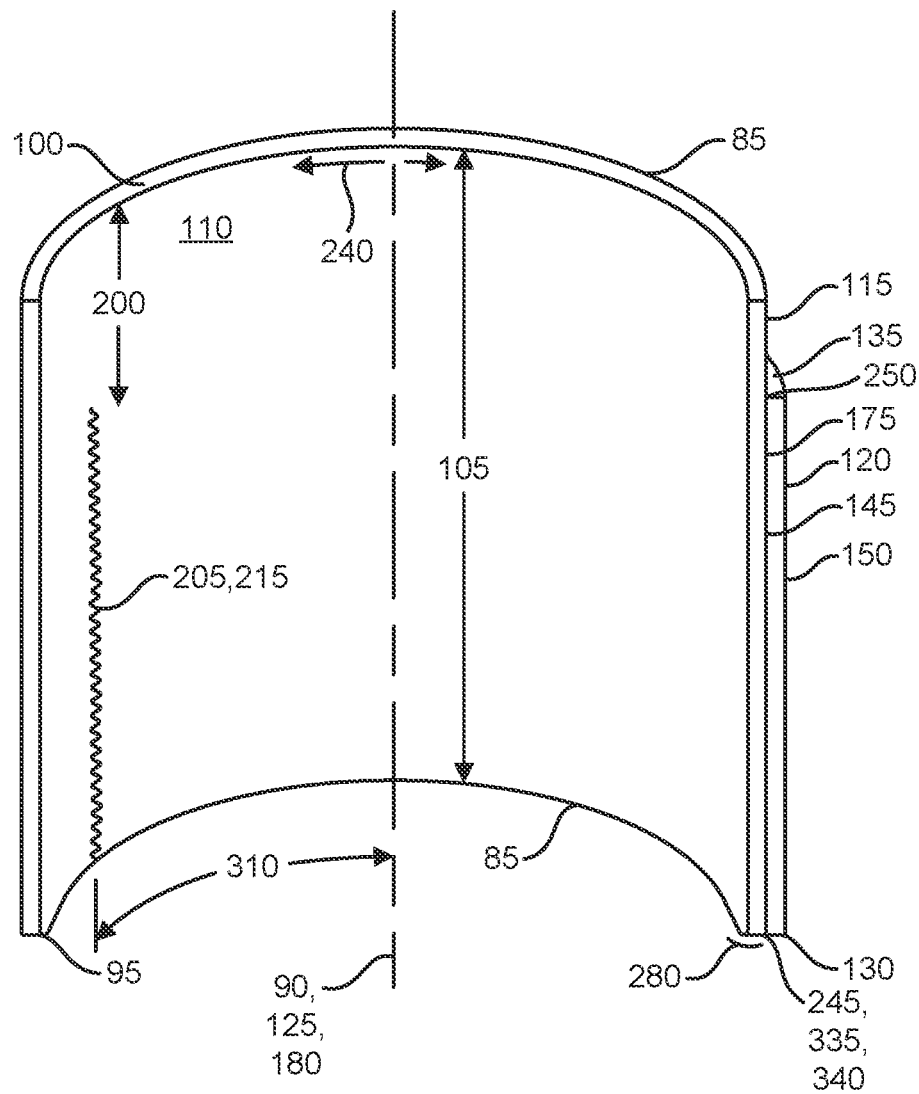

Next, FIG. 7 shows cross section cut 7-7 from FIG. 2, wherein FIG. 7 shows in detail the adjacent 175 manner and position of the first 85 and second 120 flexible elastomeric surrounding sidewalls in conjunction with the mouth 250 plus the first 95 and second 130 primary end portions with the third means 245 for attachment and the offset 285 at the opening mouth 250 being adjacent 175 to one another at the first 100 and second 135 secondary end portions, in addition to the first distance 105 is shown, plus the positioning 200 in-between of the subsequent linear section 185 to the first primary end portion 95 and the first secondary end portion 100.

Figure 8:
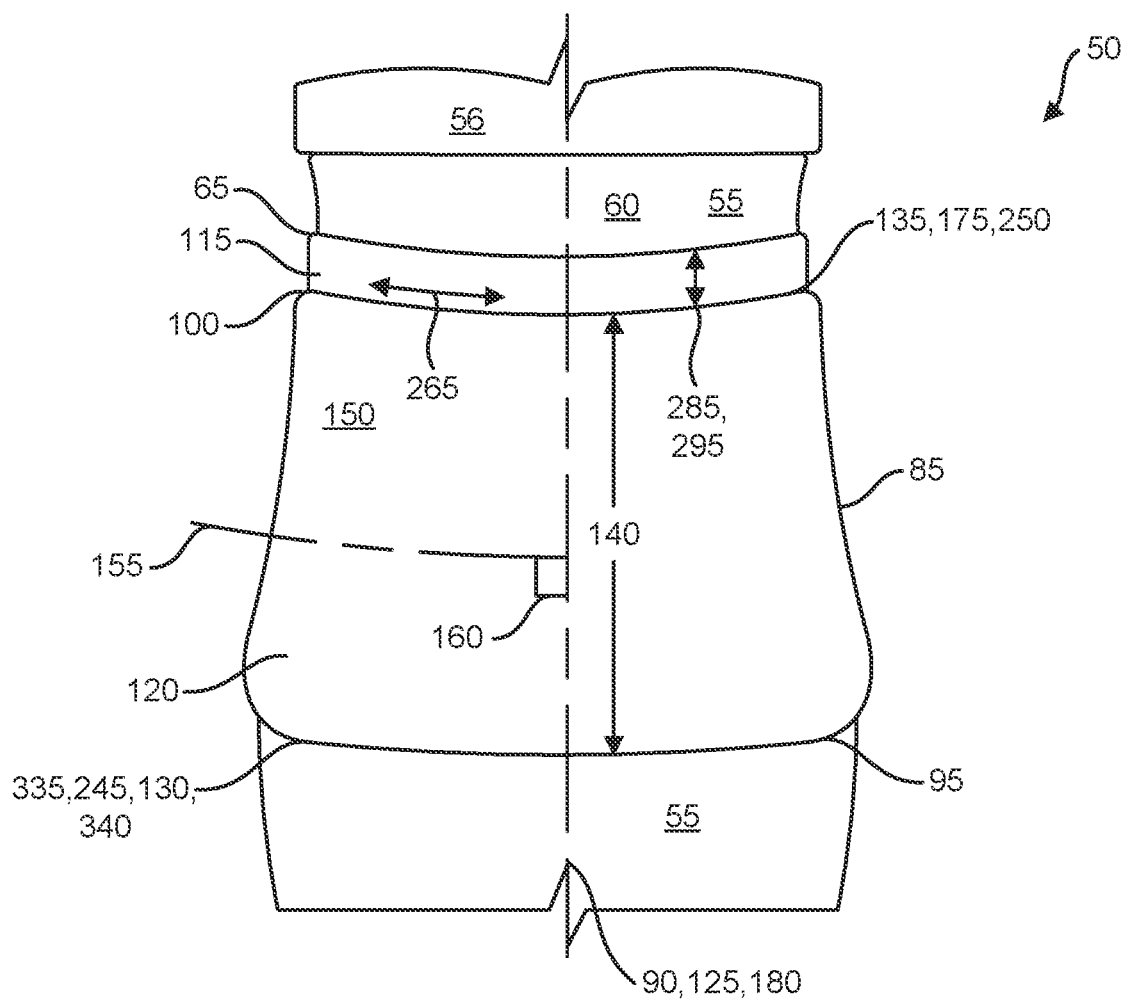
FIG. 8 shows a side elevation view of a use view of the body support wrap disposed on and elastically encompassing the user body article being the user's torso, wherein shown is the first and second flexible elastomeric surrounding sidewalls in conjunction with the mouth plus the first and second primary end portions with the third means for attachment and the offset at the opening mouth being adjacent to one another at the first and second secondary end portions, in addition the second distance is shown, plus the open interior along the mouth.

Further, FIG. 8 shows a side elevation view of a use view of the body support wrap 50 disposed on and elastically encompassing 65 the user 55 body article 60 being the user's 55 torso, wherein shown is the first 85 and second 120 flexible elastomeric surrounding sidewalls in conjunction with the mouth 250 plus the first 95 and second 130 primary end portions with the third means 245 for attachment and the offset 285 at the opening mouth 250 being adjacent 175 to one another at the first 100 and second 135 secondary end portions, in addition the second distance 140 is shown, plus the open 265 interior 255 along the mouth 250.

Figure 9:
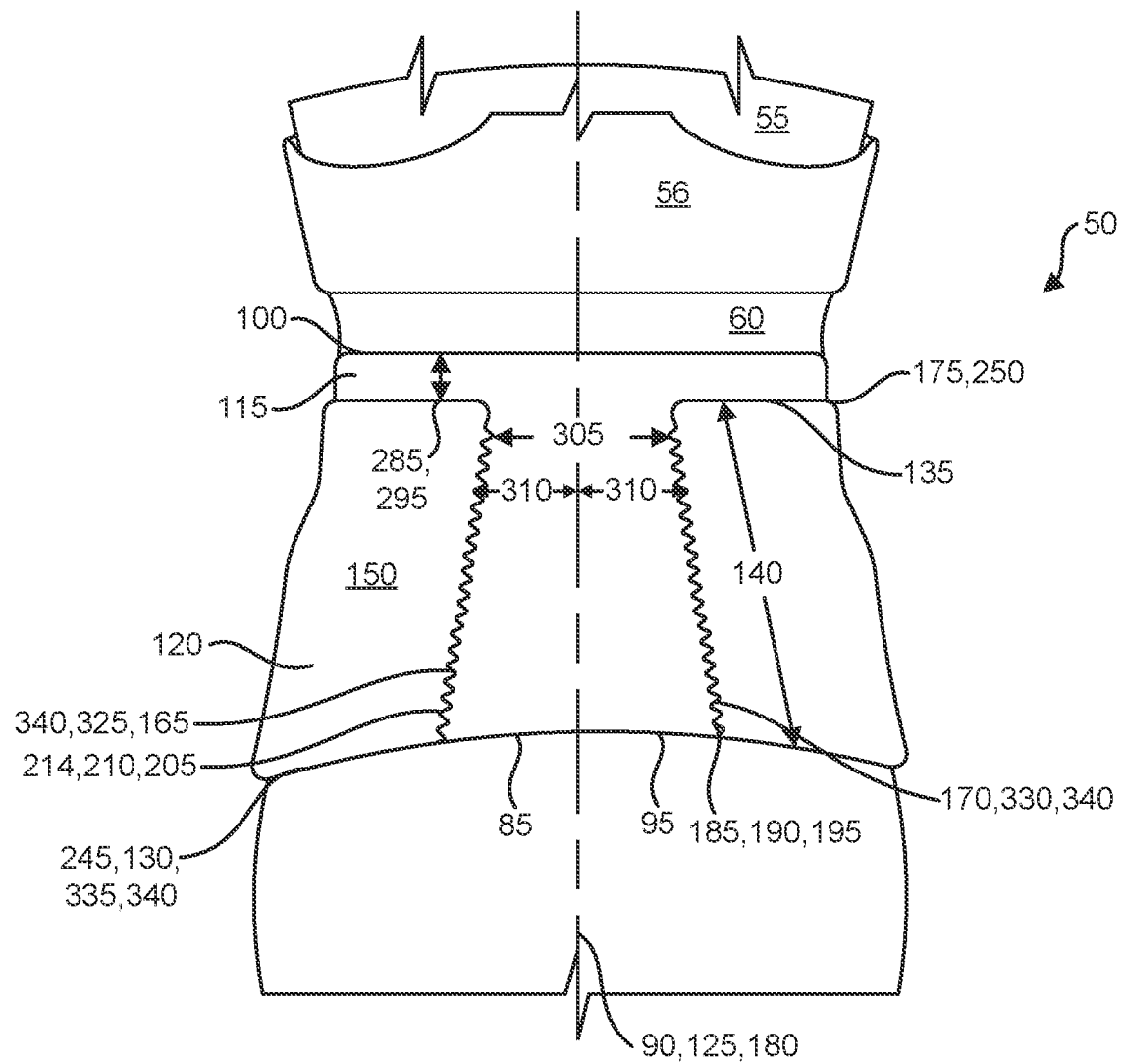

Moving onward, FIG. 9 shows a reverse side elevation view of FIG. 8, wherein FIG. 9 shows a use view of the body support wrap 50 disposed on and elastically encompassing 65 the user 55 body article 60 being the user's 55 torso, wherein shown is the first 85 and second 120 flexible elastomeric surrounding sidewalls in conjunction with the mouth 250 plus the first 95 and second 130 primary end portions with the third means 245 for attachment and the offset 285 at the opening mouth 250 being adjacent 175 to one another at the first 100 and second 135 secondary end portions. In addition, in FIG. 9 the initial 185 and subsequent 205 linear sections are shown with the second distance 140 is shown along with the fifth distance 295 being the offset 285 leading to the open 285 interior 255 along the mouth 250.

Figure 10:
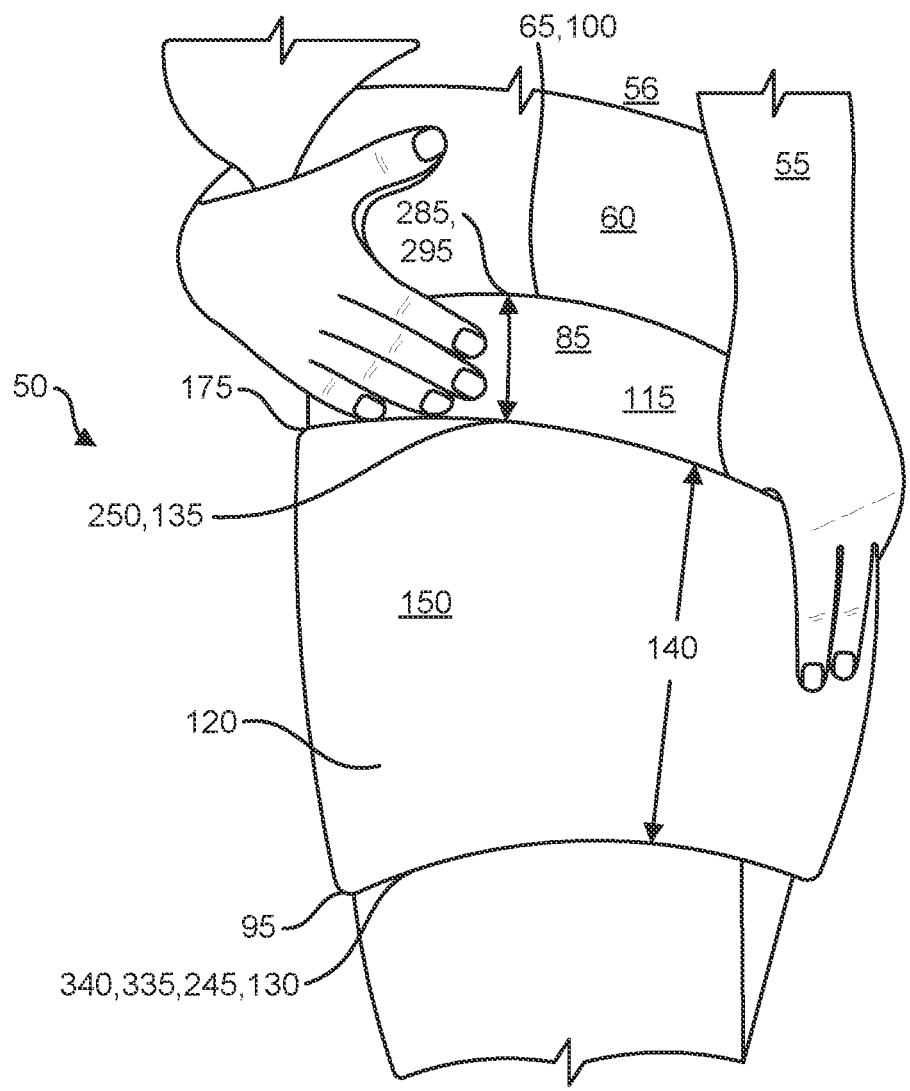
FIG. 10 shows a user left side elevation view, that shows a use view of the body support wrap disposed on and elastically encompassing the user body article being the user's torso, wherein shown is the first and second flexible elastomeric surrounding sidewalls being adjacent to one another in conjunction with the mouth plus the first and second primary end portions with the third means for attachment and the offset being the fifth distance at the opening mouth with the first and second flexible elastomeric surrounding sidewalls being adjacent to one another at the first and second secondary end portions, with the second distance is shown in relation to the fifth distance being the offset leading to the open interior along the mouth.

Continuing, FIG. 10 shows a user 55 left side elevation view, that shows a use view of the body support wrap 50 disposed on and elastically encompassing 65 the user 55 body article 60 being the user's 55 torso, wherein shown is the first 85 and second 120 flexible elastomeric surrounding sidewalls being adjacent 175 to one another in conjunction with the mouth 250 plus the first 95 and second 130 primary end portions with the third means 245 for attachment and the offset 285 being the fifth distance 295 at the opening 285 mouth 250 with the first 85 and second 120 flexible elastomeric surrounding sidewalls being adjacent 175 to one another at the first 100 and second 135 secondary end portions, with the second distance 140 is shown in relation to the fifth distance 295 being the offset 285 leading to the open 285 interior 255 along the mouth 250.

Figure 11:
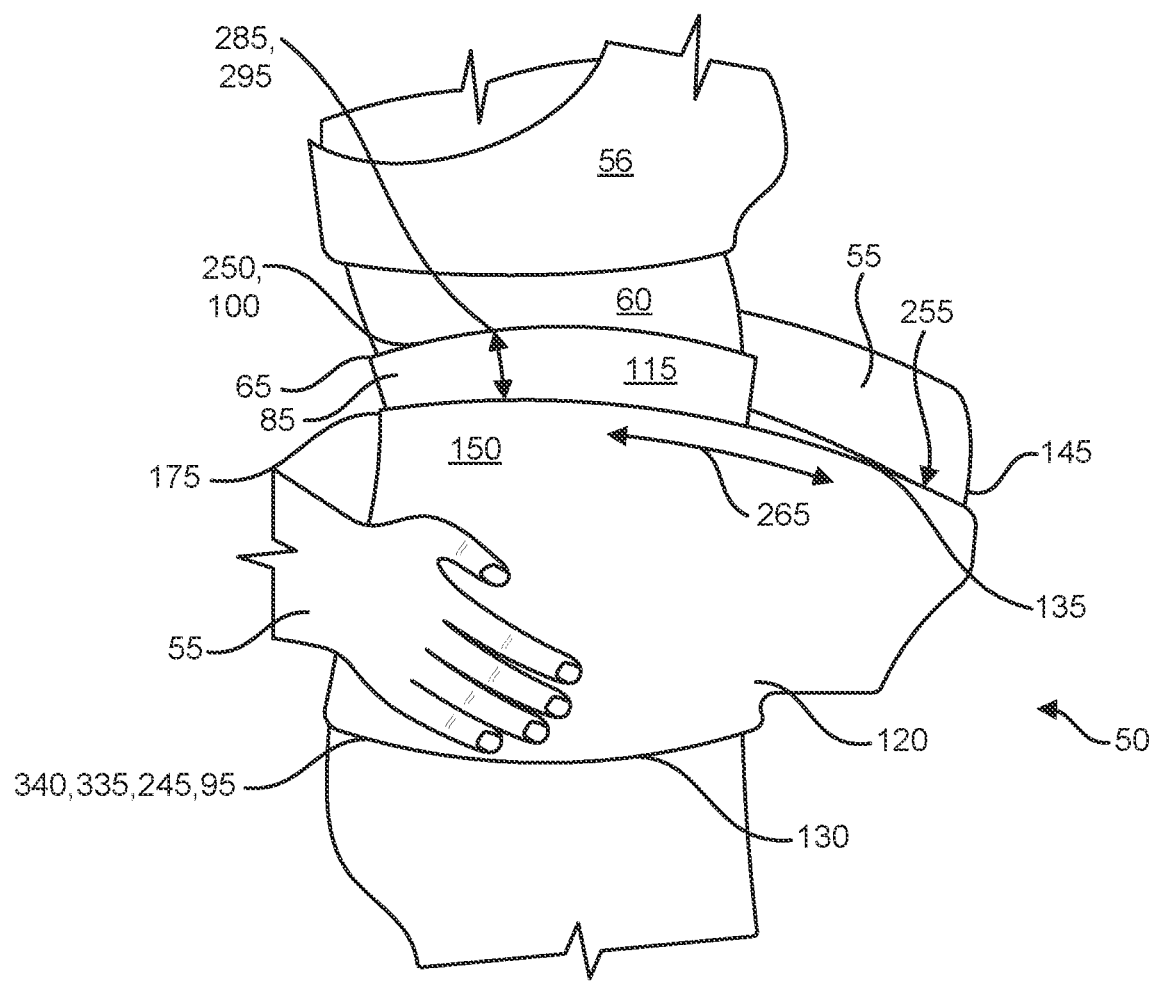
FIG. 11 shows a user right side elevation view, that shows a use view of the body support wrap disposed on and elastically encompassing the user body article being the user's torso, wherein shown is the first and second flexible elastomeric surrounding sidewalls being adjacent to one another in conjunction with the mouth being elastically opened to expose the pocket interior with the user's left hand, essentially showing the open interior along the fourth distance being from the initial linear section to the subsequent linear section, see FIGS. 3 and 4, returning to FIG. 11, also shown are the first and second primary end portions with the third means for attachment and the offset being the fifth distance at the opening mouth with the first and second flexible elastomeric surrounding sidewalls being adjacent to one another at the first and second secondary end portions with the offset at the mouth with the fifth distance, as the fifth distance being the offset leading to the open interior along the mouth.

Continuing, FIG. 11 shows a user 55 right side elevation view, that shows a use view of the body support wrap 50 disposed on and elastically encompassing 65 the user body article 60 being the user's 55 torso, wherein shown is the first 85 and second 120 flexible elastomeric surrounding sidewalls being adjacent 175 to one another in conjunction with the mouth 250 being elastically opened to expose the pocket interior 255 with the user's 55 left hand, essentially showing the open interior 255 along the fourth distance 230 being from the initial linear section 185 to the subsequent linear section 205, see FIGS. 3 and 4. Returning to FIG. 11, also shown are the first 95 and second 130 primary end portions with the third means 245 for attachment and the offset 285 being the fifth distance 295 at the opening mouth 250 with the first 85 and second 120 flexible elastomeric surrounding sidewalls being adjacent 175 to one another at the first 100 and second 135 secondary end portions with the offset 285 at the mouth 250 with the fifth distance 295, as the fifth distance 295 being the offset 285 leading to the open 285 interior 255 along the mouth 250.

Figure 12:
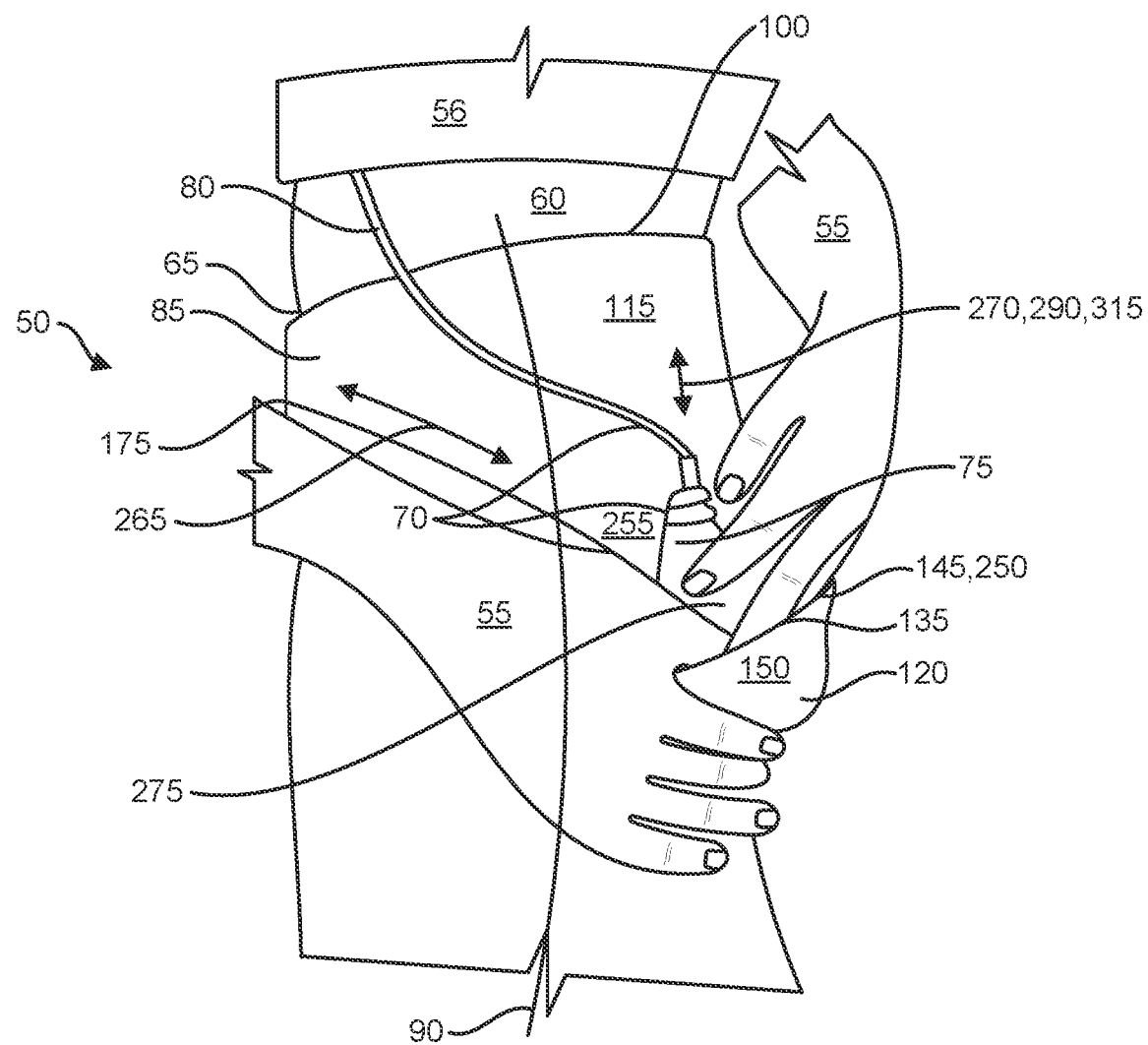
FIG. 12 shows a user right side elevation view, that shows a use view of the body support wrap disposed on and elastically encompassing the user body article being the user's torso, wherein shown is the first and second flexible elastomeric surrounding sidewalls being adjacent to one another in conjunction with the mouth being elastically opened to expose the pocket interior with the user's left hand, thereby disposing with movement the fluid communication element therein the pocket interior, wherein the fluid communication element can be disposed anywhere along the fourth distance being from the initial linear section to the subsequent linear section for user convenience and comfort, see FIGS. 3 and 4, essentially showing the open interior along the fourth distance being from the initial linear section to the subsequent linear section, again see FIGS. 3 and 4, returning to FIG. 12, showing the first and second flexible elastomeric surrounding sidewalls being adjacent to one another at the first and second secondary end portions with the offset at the mouth with the fifth distance, as the fifth distance being the offset leading to the open interior along the mouth.

Further, FIG. 12 shows a user 55 right side elevation view, that shows a use view of the body support wrap 50 disposed on and elastically encompassing 65 the user body article 60 being the user's 55 torso, wherein shown is the first 85 and second 120 flexible elastomeric surrounding sidewalls being adjacent 175 to one another in conjunction with the mouth 250 being elastically opened to expose the pocket interior 255 with the user's 55 left hand, thereby disposing with movement 290 the fluid communication element 70 therein the pocket interior 255, wherein the fluid communication element 70 can be disposed anywhere along the fourth distance 230 being from the initial linear section 185 to the subsequent linear section 205 for user convenience and comfort, see FIGS. 3 and 4, essentially showing the open interior 255 along the fourth distance 230 being from the initial linear section 185 to the subsequent linear section 205, again see FIGS. 3 and 4. Returning to FIG. 12, shown is the first 85 and second 120 flexible elastomeric surrounding sidewalls being adjacent 175 to one another at the first 100 and second 135 secondary end portions with the offset 285 at the mouth 250 with the fifth distance 295, as the fifth distance 295 being the offset 285 leading to the open 285 interior 255 along the mouth 250.

Figure 13:
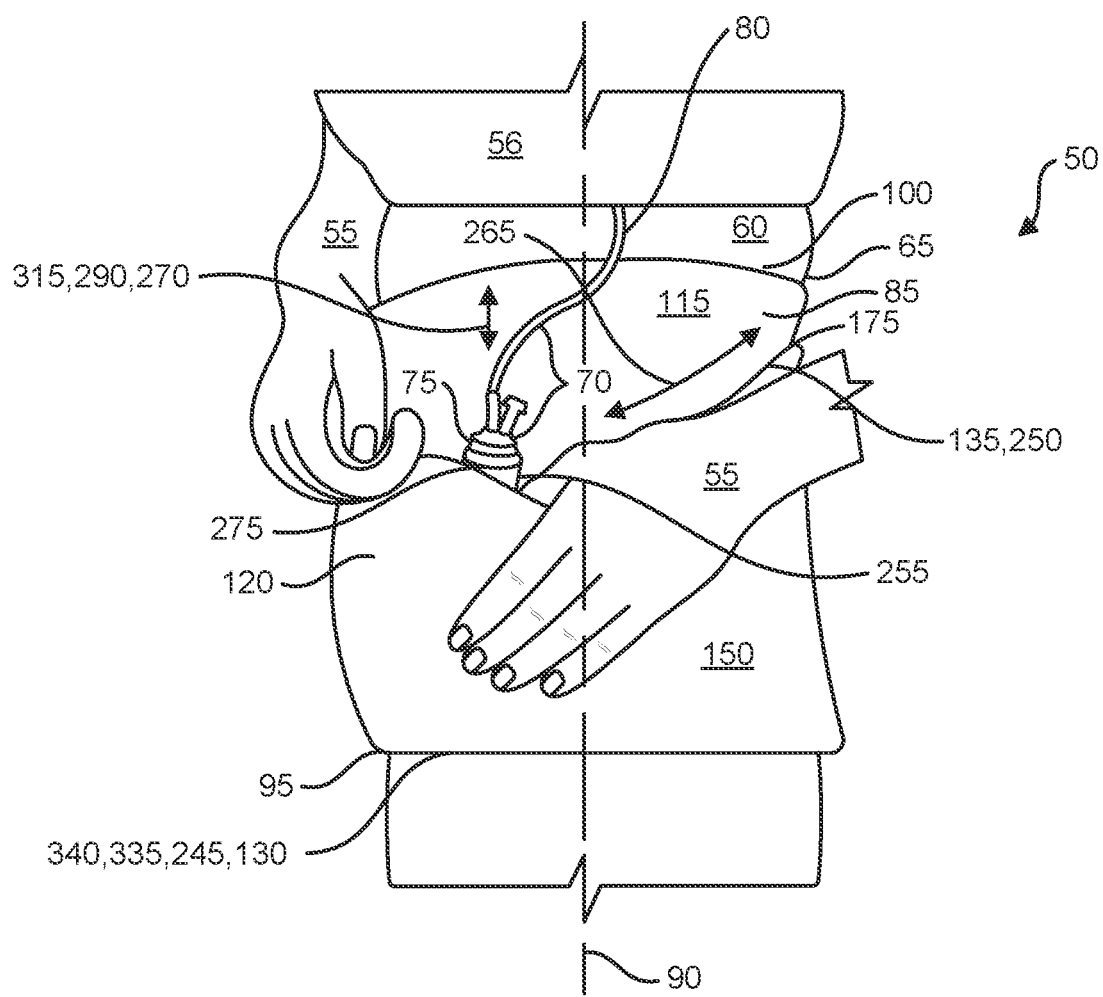
FIG. 13 shows a user front side elevation view, that shows a use view of the body support wrap disposed on and elastically encompassing the user body article being the user's torso, wherein shown is the first and second flexible elastomeric surrounding sidewalls being adjacent to one another in conjunction with the mouth being elastically opened to expose the pocket interior with the user's left and right hands, thereby disposing with movement the fluid communication element therein the pocket interior, wherein the fluid communication element can be disposed anywhere along the fourth distance being from the initial linear section to the subsequent linear section for user convenience and comfort, see FIGS. 3 and 4, essentially showing the open interior along the fourth distance being from the initial linear section to the subsequent linear section, again see FIGS. 3 and 4, returning to FIG. 13, showing the first and second flexible elastomeric surrounding sidewalls being adjacent to one another at the first and second secondary end portions with the offset at the mouth with the fifth distance, as the fifth distance being the offset leading to the open interior along the mouth.

Next, FIG. 13 shows a user 55 front side elevation view, that shows a use view of the body support wrap 50 disposed on and elastically encompassing 65 the user body article 60 being the user's 55 torso, wherein shown is the first 85 and second 120 flexible elastomeric surrounding sidewalls being adjacent 175 to one another in conjunction with the mouth 250 being elastically opened to expose the pocket interior 255 with the user's 55 left and right hands, thereby disposing with movement 290 the fluid communication element 70 therein the pocket interior 255. Wherein FIG. 13 shows the fluid communication element 70 can be disposed anywhere along the fourth distance 230 being from the initial linear section 185 to the subsequent linear section 205 for user 55 convenience and comfort, see FIGS. 3 and 4, essentially showing the open 285 interior 255 along the fourth distance 230 being from the initial linear section 185 to the subsequent linear section 205, again see FIGS. 3 and 4. Returning to FIG. 13, showing the first 85 and second 120 flexible elastomeric surrounding sidewalls being adjacent 175 to one another at the first 100 and second 135 secondary end portions with the offset 285 at the mouth 250 with the fifth distance 295, as the fifth distance 295 being the offset 285 leading to the open 285 interior 255 along the mouth 250.

Figure 14:
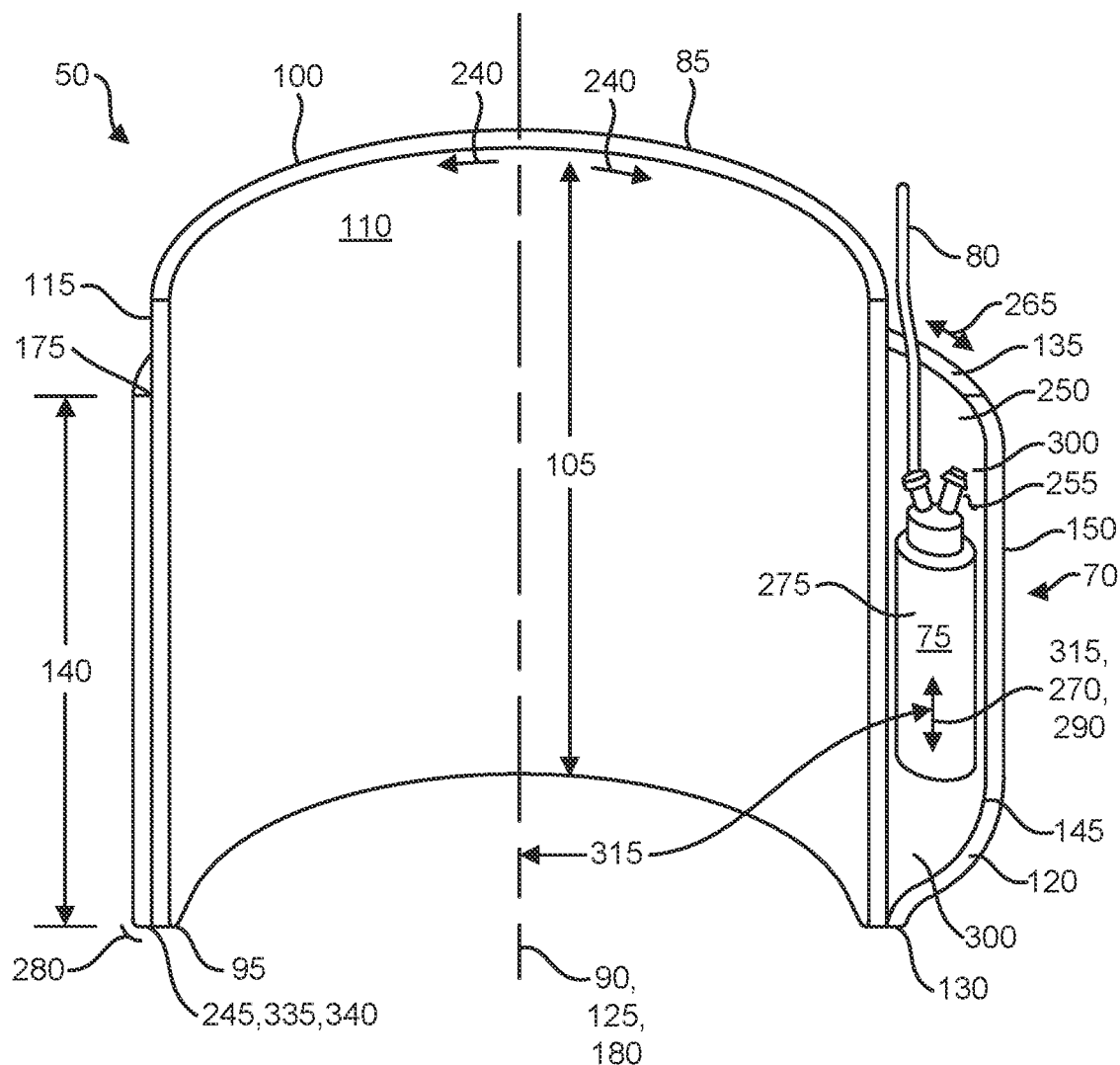
Figure 15:
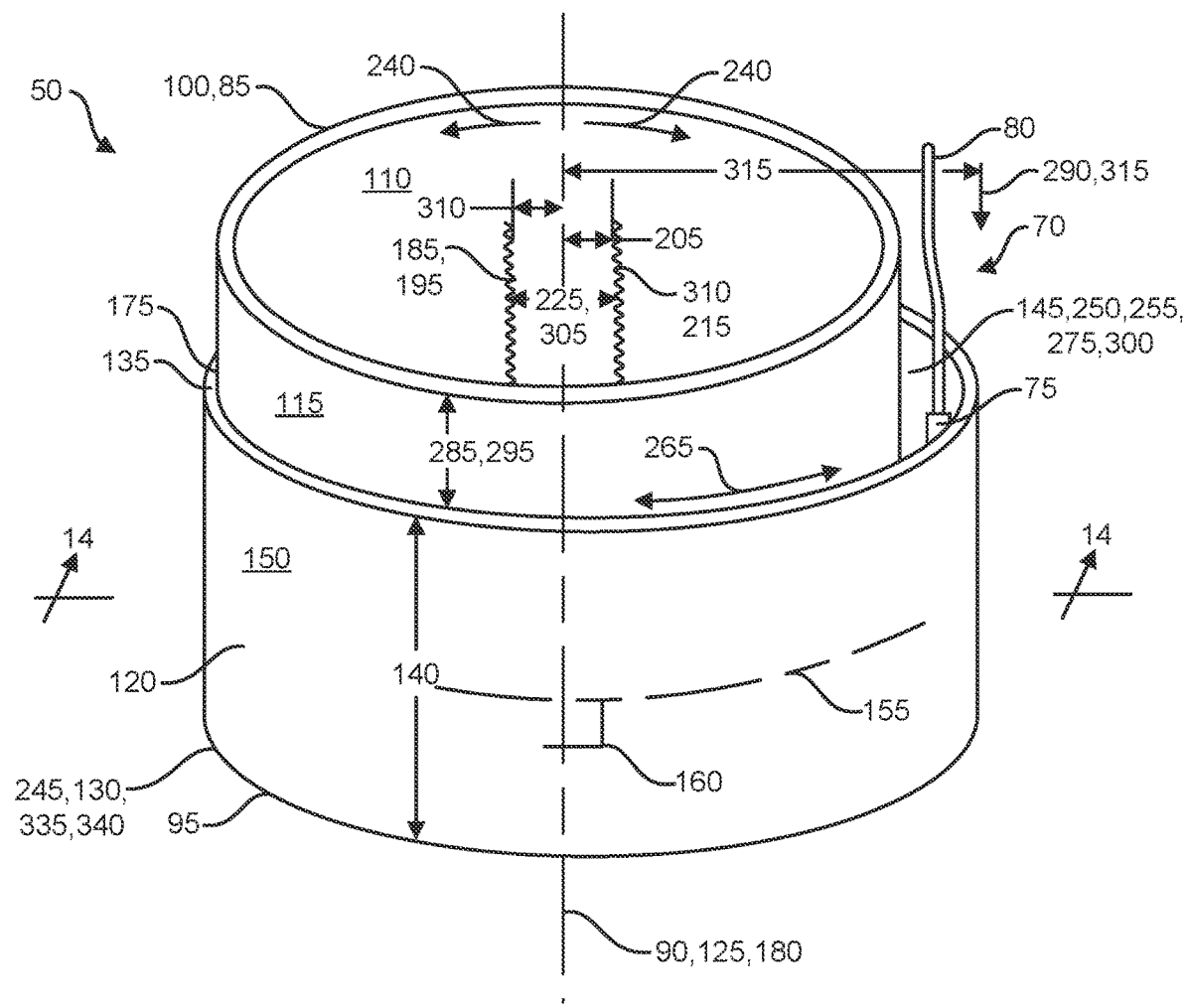
FIG. 15 shows an upper perspective view of the body support wrap that includes the mouth as between the first and second flexible elastomeric surrounding sidewalls, wherein the mouth leads to the open interior with the fluid communication element disposed therein, basically the outside view of FIG. 14, returning to FIG. 15, further shown is the offset opening of the mouth along with the initial and subsequent linear sections being partially shown, in addition the third and fourth distances are shown in their relation to one another that is only partially shown, plus the interior pocket elastically encompassing the fluid communication element via both the first and second flexible elastomeric surrounding sidewalls to hold the fluid communication element in any user desired selected position both along the second distance (vertically) and anywhere along the fourth distance (circumferentially about the longitudinal axis, see FIGS. 2, 3, and 4) for a higher degree of user convenience and comfort.

Further, FIG. 14 shows cross section cut 14-14 from FIG. 15, wherein FIG. 14 shows in cross sectional detail the adjacent 175 manner and position of the first 85 and second 120 flexible elastomeric surrounding sidewalls in conjunction with the mouth 250 plus the first 95 and second 130 primary end portions with the third means 245 for attachment and the offset 285 at the opening 285 mouth 250 being adjacent 175 to one another at the first 100 and second 135 secondary end portions, in addition to the first 105 and second 140 distances are shown of the first 85 and second 120 flexible elastomeric surrounding sidewalls. Plus shown in FIG. 14 the interior pocket 255 elastically encompassing 65 the fluid communication element 70 via both the first 85 and second 120 flexible elastomeric surrounding sidewalls to hold the fluid communication element 70 in any user 55 desired selected position both along the second distance 140 (vertically) and anywhere along the fourth distance 230 (circumferentially about the longitudinal axis, see FIGS. 2, 3, and 4) for a higher degree of user 55 convenience and comfort.

Continuing, FIG. 15 shows an upper perspective view of the body support wrap 50 that includes the mouth 250 as between the first 85 and second 120 flexible elastomeric surrounding sidewalls, wherein the mouth 250 leads to the open interior 255 with the fluid communication element 70 disposed therein, basically the outside view of FIG. 14. Returning to FIG. 15, further shown is the offset opening 285 of the mouth 250 along with the initial 185 and subsequent 205 linear sections being partially shown, in addition the third 225 and fourth 230 distances are shown in their relation to one another that is only partially shown, plus the interior pocket 255 elastically encompassing 65 the fluid communication element 70 via both the first 85 and second 120 flexible elastomeric surrounding sidewalls to hold the fluid communication element 70 in any user 55 desired selected position both along the second distance 140 (vertically) and anywhere along the fourth distance 230 (circumferentially about the longitudinal axis, see FIGS. 2, 3, and 4) for a higher degree of user 55 convenience and comfort.

Figure 16:
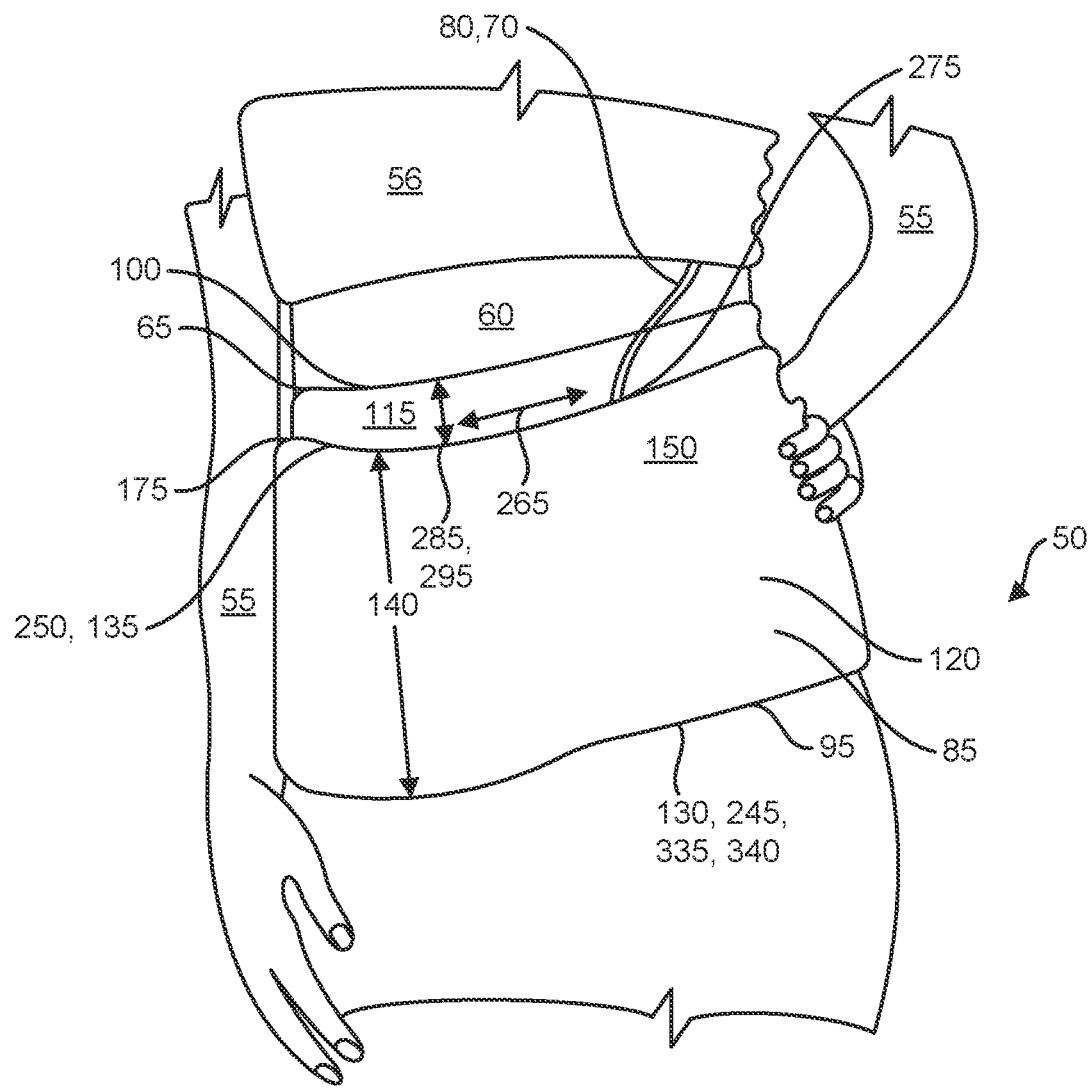
FIG. 16 shows a user front side elevation view, that shows a use view of the body support wrap disposed on and elastically encompassing the user body article being the user's torso, wherein shown is the first and second flexible elastomeric surrounding sidewalls being adjacent to one another in conjunction with the mouth being elastically opened to pass through the tubing from the fluid communication element disposed therein the pocket interior, wherein the fluid communication element can be disposed anywhere along the fourth distance, see FIGS. 2, 3, and 4, being from the initial linear section to the subsequent linear section for user convenience and comfort, returning to FIG. 16, showing the first and second flexible elastomeric surrounding sidewalls being adjacent to one another at the first and second secondary end portions with the offset at the mouth with the fifth distance, as the fifth distance being the offset leading to the open interior along the mouth.

In addition, FIG. 16 shows a user 55 front side elevation view, that shows a use view of the body support wrap 50 disposed on and elastically encompassing 65 the user 55 body article 60 being the user's 55 torso, wherein shown is the first 85 and second 120 flexible elastomeric surrounding sidewalls being adjacent 175 to one another in conjunction with the mouth 250 being elastically opened to pass through the tubing 80 from the fluid communication element 70 disposed therein the pocket interior 255, wherein the fluid communication element 70 can be disposed anywhere along the fourth distance 230, see FIGS. 2, 3, and 4, being from the initial linear section 185 to the subsequent linear section 205 for user 55 convenience and comfort. Returning to FIG. 16, showing the first 85 and second 120 flexible elastomeric surrounding sidewalls being adjacent 175 to one another at the first 100 and second 135 secondary end portions with the offset 285 at the mouth 250 with the fifth distance 295, as the fifth distance 295 being the offset 285 leading to the open interior 255 along the mouth 250.

Broadly, in looking at FIGS. 1 to 16, the present invention is the body support wrap 50 adapted to encompass 65 the body article 60 of a user 55 while elastically encompassing 65 and supporting the fluid communication element 70, the body support wrap 50 includes the first flexible elastomeric surrounding sidewall 85 that is about a longitudinal axis 90, the first flexible elastomeric surrounding sidewall 85 having the first primary end portion 95 and an opposing first secondary end portion 100 with the longitudinal axis 90 spanning therebetween, having the first distance 105 as between the first primary end portion 95 and the first secondary end portion 100, the first flexible elastomeric surrounding sidewall 85 further including a first inner surface 110 and an opposing first outer surface 115, see in particular FIGS. 1 to 7.

Further included in the body support wrap 50 is the second flexible elastomeric partial surrounding sidewall 120 that is partially about a longwise axis 125, the second flexible elastomeric surrounding sidewall 120 having the second primary end portion 130 and an opposing second secondary end portion 135 with the longwise axis 125 spanning therebetween, having the second distance 140 as between the second primary end portion 130 and the second secondary end portion 135, the second flexible elastomeric surrounding sidewall 120 further including a second inner surface 145 and an opposing second outer surface 150. Additionally, the second flexible elastomeric partial surrounding sidewall 120 includes a lengthwise axis 155 that is perpendicularly positioned 160 to the longwise axis 125, further the second flexible elastomeric partial surrounding sidewall 120 includes a second principal margin 165 and an opposing second subordinate margin 170 with the lengthwise axis 155 spanning therebetween, wherein the second inner surface 145 is positioned adjacent 175 to a portion of the first outer surface 115 to position the longitudinal axis 90 and said longwise axis 125 to be co-incident 180 to one another, again see in particular FIGS. 1 to 7.

Also included in the body support wrap 50 is a first means 195 for attachment of the second principal margin 165 to the initial linear section 185 that is disposed 190 on the first outer surface 115 and the initial linear section 185 is positioned 200 in-between the first primary end portion 95 and the first secondary end portion 100 and a second means 215 for attachment of the second subordinate margin 170 to the subsequent linear section 205 disposed 210 on the first outer surface 115 and the subsequent linear section 205 is positioned 220 in-between the first primary end portion 95 and the first secondary end portion 100. Further the lesser third distance 225 is formed as between the initial linear section 185 and the subsequent linear section 205 along the first outer surface 115 and the greater 235 fourth distance 230 is formed as between the initial linear section 185 and the subsequent linear section 205 along the first outer surface 115 due to the first flexible elastomeric surrounding sidewall 85 being about 240 the longitudinal axis 90 resulting in the third 225 and fourth 230 distances as between the initial linear section 185 and the subsequent linear section 205 along the first outer surface 115, again see in particular FIGS. 1 to 7.

The body support wrap 50 also has a third means 245 for attachment of the second primary end portion 130 and the first primary end portion 95 along the fourth distance 230, wherein the mouth 250 is formed as between the first secondary end portion 100 and the second secondary end portion 135 along the fourth distance 230 being from the initial linear section 185 to the subsequent linear section 205. Further an open 285 interior 255 is formed as between the first flexible elastomeric surrounding sidewall 85 first outer surface 115 and the second flexible elastomeric partial surrounding sidewall 120 second inner surface 145 plus as between the first 195, second 215, and third 245 means for attachment, again see in particular FIGS. 1 to 7. Wherein operationally the fluid communication element 70 is passed therethrough 270 the mouth 250 and stored 275 in the open 285 interior 255 with the first flexible elastomeric surrounding sidewall 85 encompassing 65 the body article 60 to ultimately hold the fluid communication element 70 is a selected position as against the body article 60, see FIGS. 12 to 16.

Alternatively for the body support wrap 50 the second distance 140 can be less that the first distance 105 and with the third means 245 for attachment of the second primary end portion 130 and the first primary end portion 95 along the fourth distance 230 being structurally positioned such that the second primary end portion 130 and the first primary end portion 95 are positioned juxtapose 280 to one another structurally resulting in the mouth 250 having an offset 285 opening by the second distance 140 being less than the first distance 105, operationally allowing for the fluid communication element 70 to be slid down 290 the first outer surface 115 therethrough the mouth 250 proceeding into the open 285 interior 255 in an easier manner due the offset 285 allowing easier mouth 250 opening, see in particular FIGS. 12 to 16.

Further alternatively for the body support wrap 50 with the second distance 140 being less that the first distance 105 forms a fifth differential distance 295 that is in-between the first 105 and second 140 distances, wherein the fifth differential distance 295 is in the range of approximately one-eighth inch to ten inches to further facilitate the fluid communication element 70 to be slid down 290 the first outer surface 115 therethrough the mouth 250 proceeding into the open interior 255 in a further easier manner, see in particular FIGS. 1, 2, 8, 11, 15, and 16.

Optionally for the body support wrap 50 with the third distance 225 being less than the fourth distance 230 forms a percentage ratio of the third distance 225 to the fourth distance 230 that is in the range of approximately ten percent to ninety percent to operationally facilitate the open 285 interior 255 to be a desired volumetric size 300 for the fluid communication element 70, see FIG. 14.

Another option for the body support wrap 50 is where the initial linear section 185 and the subsequent linear section 205 are positioned parallel 305 to one another for the open 285 interior 255 to be consistent in shape, see FIGS. 1, 2, and 9.

Further optionally for the body support wrap 50 is where the initial linear section 185 and the subsequent linear section 205 being positioned parallel 305 to one another are also both parallel 310 to the longitudinal axis 90 thus resulting in the first 195 and second 215 attachment means being parallel 310 to one another and parallel 310 to the longitudinal axis 90, operationally resulting in disposing 315 the fluid communication element 70 therethrough the mouth 250 and into the open 285 interior 255 in a manual movement 290, 315 that is parallel 315 to the longitudinal axis 90 for ease of disposing the fluid communication element 70 into the open 285 interior 255, see FIGS. 1, 2, 9, 12, 13, and 15.

Yet another option for the body support wrap 50 wherein the first 85 and second 120 flexible elastomeric surrounding sidewalls are preferably constructed of a combination of nylon and spandex to give an omnidirectional stretch 320 of the first 85 and second 120 flexible elastomeric surrounding sidewalls along the longitudinal 90, longwise 125, and lengthwise 155 axes for operationally better encompassing 65 of the body article 60 by the first 85 and second 120 flexible elastomeric surrounding sidewalls in addition to an encompassing 65 retaining of the fluid communication element 70 into the open 285 interior 255, see FIGS. 1, 5, and FIGS. 10 to 15.

Continuing on options for the body support wrap 50 wherein the first 195, second 215, and third 245 means for attachment are preferably constructed of surface flush stretch stitching 325, 330, 335 for the first, second, and third surface flush stretch stitching respectively, to operationally minimize any protruding ridge 340 that would be adjacent to the body article 60 for comfort of the user 55, wherein the surface flush stretch stitching 325, 330, 335 is defined to minimize the protrusion ridge 340 on the first inner surface 110, first outer surface 115, second inner surface 145, and the second outer surface 150, see FIGS. 1 to 4, 6, 7, and 9.

Preferred body support wrap 50 specifics include an overall length distance 105, see FIG. 2, is about 12" long in total coverage of user 55 body article 60 and can be worn around hips or in any variety of folds per the patient's comfort as the first 85 and second 120 flexible fabric panel sidewalls are easily foldable, see FIGS. 8 to 16, wherein the first distance 105 is preferably 12" wide also when laid flat. Further the first secondary end portion 100 can have a reinforced top 1.5" in height to prevent rolling of the secondary end portion 100 down the body article 60. Also preferably the fourth distance 230 is about 20" and the third distance 225 is about 4", see FIG. 2, allowing for maximum flexibility in body support wrap 50 placement about the body article 60, plus further the second distance 140 is about 10", again see FIG. 2.

The second secondary end portion 135 preferably has an offset lip at the mouth 250 of the interior 255, wherein the lip is about 1" in height to securely hold tubing 80 and reservoirs 75 within the interior 255, see FIG. 14, in addition this also aids in ease of use as the interior 255 is easily identifiable and easy to access on the user's 55 body article 60 therethrough the open 285 mouth 250, see FIGS. 10 to 13.

The first 85 and second 120 flexible fabric panel sidewalls are preferably constructed of an antimicrobial fabric designed to prevent the growth of bacteria and odor from drainage fluids and constant wear, this is distinctly different from the current prior art cotton-blend mastectomy tops worn as a clothing item. Further, the first 85 and second 120 flexible fabric panel sidewalls are preferably a synthetic elastic fabric blend retains shape for long-wearing security of postsurgical body support wrap 50 and is sewn with elasticated four-way or omni-directional 320 stretch with stretch 325, 330, 335, stitching with elasticized thread to maximize stretch through the user's 50 body article 60 as well as through the wrap-around interior 255 technology, in addition the first 85 and second 120 flexible fabric panel sidewalls can be made of either fabric or disposable hygienic materials for both multiple use (wash and wear) or single use applications, see FIGS. 1, 14, and 15.

The open interior 265 wide-sleeve and seamless pocket interior 255 enables flexibility in the placement of recovery apparatus or the fluid communication element 70 while ensuring a secure hold 275 no matter the positioning of the fluid communication element 70 allowing for maximum user 55 comfort, see FIGS. 12 to 16, that is opposed to the prior art having fixed and limited size pockets for the fluid communication element 70 that restricts placement and flexibility of the fluid communication element 70 in relation to the user's 55 body article 60

Similar embodiments of the body support wrap 50 are also conceivable, which could vary in size, construction or configuration to fit a user's 50 limbs or other body appendages being body articles 60 for similar purposes, as the body support wrap 50 can be worn comfortably for extended periods of time, enabling the user 50 and caregivers to remove and replace bandages, reposition or work with medical apparatus-being the fluid communication element 70, within the pocket interior 255 wide mouth 250 open interior 265 without necessitating removal of the body support wrap 50, thus minimizing the aggravation of sensitive skin areas on the user 50 body article 60. While the primary purpose this invention is to meet the needs of user 50 patients recovering from surgery, it is conceivable that the body support wrap 50 can be useful in other applications such as to hold tools, money, other implements or devices to a user 55 body article 60.

CONCLUSION

Accordingly, the present invention of a body support wrap has been described with some degree of particularity directed to the embodiments of the present invention. It should be appreciated, though; that the present invention is defined by the following claims construed in light of the prior art so modifications of the changes may be made to the exemplary embodiments of the present invention without departing from the inventive concepts contained therein.

The invention claimed is:

1. A body support wrap adapted to encompass a body article of a user while elastically encompassing and supporting a fluid communication element, said body support wrap comprising:
    (a) a first flexible elastomeric surrounding sidewall that is about a longitudinal axis, said first flexible elastomeric surrounding sidewall having a first primary end portion and an opposing first secondary end portion with said longitudinal axis spanning therebetween, having a first distance as between said first primary end portion and said first secondary end portion, said first flexible elastomeric surrounding sidewall further including a first inner surface and an opposing first outer surface;
    (b) a second flexible elastomeric partial surrounding sidewall that is partially about a longwise axis, said second flexible elastomeric surrounding sidewall having a second primary end portion and an opposing second secondary end portion with said longwise axis spanning therebetween, having a second distance as between said second primary end portion and said second secondary end portion, said second flexible elastomeric surrounding sidewall further including a second inner surface and an opposing second outer surface, additionally, said second flexible elastomeric partial surrounding sidewall includes a lengthwise axis that is perpendicularly positioned to said longwise axis, further said second flexible elastomeric partial surrounding sidewall includes a second principal margin and an opposing second subordinate margin with said lengthwise axis spanning therebetween, wherein said second inner surface is positioned adjacent to a portion of said first outer surface to position said longitudinal axis and said longwise axis to be co-incident to one another;
    (c) a first means for attachment of said second principal margin to an initial linear section that is disposed on said first outer surface and said initial linear section is positioned in-between said first primary end portion and said first secondary end portion;
    (d) a second means for attachment of said second subordinate margin to a subsequent linear section disposed on said first outer surface and said subsequent linear section is positioned in-between said first primary end portion and said first secondary end portion, further a third distance is formed as between said initial linear section and said subsequent linear section along said first outer surface, said third distance is further disposed between said second principal margin and said second subordinate margin of said second flexible elastomeric partial surrounding sidewall, as said third distance has no said second inner surface positioned adjacent to said first outer surface, a fourth distance is formed as between said initial linear section and said subsequent linear section along said first outer surface due to said first flexible elastomeric surrounding sidewall being about said longitudinal axis resulting in said third and fourth distances as between said initial linear section and said subsequent linear section along said first outer surface, said fourth distance is further defined as spanning between said second principal margin and said second subordinate margin of said second flexible elastomeric partial surrounding sidewall, as said fourth distance has said second inner surface positioned adjacent to said first outer surface to form said second inner surface being positioned adjacent to said portion of said first outer surface forming said second flexible elastomeric partial surrounding sidewall, wherein said fourth distance is greater than said third distance, wherein said third distance being less than said fourth distance forms a percentage ratio of said third distance to said fourth distance that is approximately twenty percent to operationally facilitate said open interior to be a desired volumetric size for the fluid communication element, further said open interior spans along said lengthwise axis in conjunction with said fourth distance to provide said first outer surface being adjacent to said second inner surface for a majority defined as greater than fifty percent of said first flexible elastomeric surrounding sidewall along said lengthwise axis; and
    (e) a third means for attachment of said second primary end portion and said first primary end portion along said fourth distance, wherein a mouth is formed as between said first secondary end portion and said second secondary end portion along said fourth distance being from said initial linear section to said subsequent linear section, further an open interior is formed as between said first flexible elastomeric surrounding sidewall first outer surface and said second flexible elastomeric partial surrounding sidewall second inner surface plus as between said first, second, and third means for attachment, wherein operationally the fluid communication element is functionally passed therethrough said mouth and stored in said open interior with said first and second flexible elastomeric surrounding sidewalls encompassing elastically the body article to singularly hold the fluid communication element in a selected position as against the body article for any selected position of the fluid communication element along said fourth distance.

2. A body support wrap according to claim 1 wherein said second distance is less than said first distance and with said third means for attachment of said second primary end portion and said first primary end portion along said fourth distance being structurally positioned such that said second primary end portion and said first primary end portion are positioned juxtapose to one another structurally resulting in said mouth having an offset opening by said second distance being less than said first distance operationally functionally allowing for the fluid communication element to be slid down said first outer surface therethrough said mouth proceeding into said open interior, wherein said mouth and said open interior extend along an entirety of said fourth distance to facilitate user access to said open interior over a major portion of the body article along said lengthwise axis.

3. A body support wrap according to claim 2 wherein said first distance minus said second distance equals a fifth distance, such that said fifth distance is less than said first distance and said fifth distance is less than said second distance, wherein said fifth distance is approximately twenty percent of said second distance to further facilitate the fluid communication element to be slid down said first outer surface therethrough said mouth proceeding into said open interior, wherein said mouth and said open interior extend along an entirety of said fourth distance to facilitate user access to said open interior over a major portion of the body article.

4. A body support wrap according to claim 1 wherein said initial linear section and said subsequent linear section are positioned parallel to one another for said open interior to be consistent in shape.

5. A body support wrap according to claim 4 wherein said initial linear section and said subsequent linear section being positioned parallel to one another are also both parallel to said longitudinal axis thus resulting in said first and second attachment means being parallel to one another and parallel to said longitudinal axis, operationally resulting in functionally disposing the fluid communication element therethrough said mouth and into said open interior in a manual movement that is parallel to said longitudinal axis for ease of disposing the fluid communication element into said open interior.

6. A body support wrap according to claim 1 wherein said first and second flexible elastomeric surrounding sidewalls are constructed of a combination of nylon and spandex to give an omnidirectional stretch of said first and second flexible elastomeric surrounding sidewalls along said longitudinal, longwise, and lengthwise axes for operationally better encompassing of the body article by said first and second flexible elastomeric surrounding sidewalls in addition to a retaining of the fluid communication element into said open interior.

7. A body support wrap according to claim 6 wherein said first, second, and third means for attachment are constructed of a surface flush stretch stitching that has a protruding ridge, wherein to operationally minimize said protruding ridge that would be adjacent to the body article for comfort of the user, wherein said surface flush stretch stitching is defined to minimize said protruding ridge on said first and second, inner and outer surfaces.

8. A body support wrap adapted to encompass a body article of a user while elastically encompassing and supporting a fluid communication element, said body support wrap comprising:
  (a) a first flexible fabric panel surrounding sidewall that is about a longitudinal axis, said first flexible fabric panel surrounding sidewall having a first primary end portion and an opposing first secondary end portion with said longitudinal axis spanning therebetween, having a first distance as between said first primary end portion and said first secondary end portion, said first flexible fabric panel surrounding sidewall further including a first inner surface and an opposing first outer surface;
  (b) a second flexible fabric panel partial surrounding sidewall that is partially about a longwise axis, said second flexible fabric panel surrounding sidewall having a second primary end portion and an opposing second secondary end portion with said longwise axis spanning therebetween, having a second distance as between said second primary end portion and said second secondary end portion, said second flexible fabric panel surrounding sidewall further including a second inner surface and an opposing second outer surface, additionally, said second flexible fabric panel partial surrounding sidewall includes a lengthwise axis that is perpendicularly positioned to said longwise axis, further said second flexible fabric panel partial surrounding sidewall includes a second principal margin and an opposing second subordinate margin with said lengthwise axis spanning therebetween, wherein said second inner surface is positioned adjacent to a portion of said first outer surface to position said longitudinal axis and said longwise axis to be co-incident to one another;
  (c) a first surface flush stretch stitching having a protruding ridge, said first surface flush stretch stitching is for attachment of said second principal margin to an initial linear section that is disposed on said first outer surface and said initial linear section is positioned in-between said first primary end portion and said first secondary end portion;
  (d) a second surface flush stretch stitching having a protruding ridge, said second surface flush stretch stitching is for attachment of said second subordinate margin to a subsequent linear section disposed on said first outer surface and said subsequent linear section is positioned in-between said first primary end portion and said first secondary end portion, further a third distance is formed as between said initial linear section and said subsequent linear section along said first outer surface, said third distance is further disposed between said second principal margin and said second subordinate margin of said second flexible fabric panel partial surrounding sidewall, as said third distance has no said second inner surface positioned adjacent to said first outer surface, a fourth distance is formed as between said initial linear section and said subsequent linear section along said first outer surface due to said first flexible fabric panel surrounding sidewall being about said longitudinal axis resulting in said third and fourth distances as between said initial linear section and said subsequent linear section along said first outer surface, said fourth distance is further defined as spanning between said second principal margin and said second subordinate margin of said second flexible fabric panel partial surrounding sidewall, as said fourth distance has said second inner surface positioned adjacent to said first outer surface to form said second inner surface being positioned adjacent to said portion of said first outer surface forming said second flexible fabric panel partial surrounding sidewall, wherein said fourth distance is greater than said third distance, wherein said third distance being less than said fourth distance forms a percentage ratio of said third distance to said fourth distance that is approximately twenty percent to operationally facilitate said open interior to be a desired volumetric size for the fluid communication element, further said open interior spans along said lengthwise axis in conjunction with said fourth distance to provide said first outer surface being adjacent to said second inner surface for a majority defined as greater than fifty percent of said first flexible elastomeric surrounding sidewall along said lengthwise axis; and (e) a third surface flush stretch stitching having a protruding ridge, said third surface flush stretch stitching is for attachment of said second primary end portion and said first primary end portion along said fourth distance, wherein a mouth is formed as between said first secondary end portion and said second secondary end portion along said fourth distance being from said initial linear section to said subsequent linear section, further an open interior is formed as between said first flexible fabric panel surrounding sidewall first outer surface and said second flexible fabric panel partial surrounding sidewall second inner surface plus as between said first, second, and third surface flush stretch stitching for attachment, wherein operationally the fluid communication element is functionally passed therethrough said mouth and stored in said open interior with said first and second flexible fabric panel surrounding sidewalls encompassing elastically the body article to singularly hold the fluid communication element in a selected position as against the body article, for any selected position of the fluid communication element along said fourth distance, said first, second, and third surface flush stretch stitching is to operationally minimize said protruding ridge that would be adjacent to the body article for comfort of the user, wherein said first, second, and third surface flush stretch stitching is defined to minimize said protruding ridge on said first and second, inner and outer surfaces.

9. A body support wrap according to claim 8 wherein said second distance is less than said first distance and with said third surface flush stretch stitching for attachment of said second primary end portion and said first primary end portion along said fourth distance being structurally positioned such that said second primary end portion and said first primary end portion are positioned juxtapose to one another structurally resulting in said mouth having an offset opening by said second distance being less than said first distance, operationally functionally allowing for the fluid communication element to be slid down said first outer surface therethrough said mouth proceeding into said open interior, wherein said mouth and said open interior extend along an entirety of said fourth distance to facilitate user access to said open interior over a major portion of the body article along said lengthwise axis.

10. A body support wrap according to claim 9 wherein said first distance minus said second distance equals a fifth distance, such that said fifth distance is less than said first distance and said fifth distance is less than said second distance, wherein said fifth distance is approximately twenty percent of said second distance to further facilitate the fluid communication element to be slid down said first outer surface therethrough said mouth proceeding into said open interior, wherein said mouth and said open interior extend along an entirety of said fourth distance to facilitate user access to said open interior over a major portion of the body article.

11. A body support wrap according to claim 9 wherein said initial linear section and said subsequent linear section are positioned parallel to one another for said open interior to be consistent in shape.

12. A body support wrap according to claim 11 wherein said initial linear section and said subsequent linear section being positioned parallel to one another are also both parallel to said longitudinal axis thus resulting in said first and second surface flush stretch stitching being parallel to one another and parallel to said longitudinal axis, operationally resulting in functionally disposing the fluid communication element therethrough said mouth and into said open interior in a manual movement that is parallel to said longitudinal axis for ease of disposing the fluid communication element into said open interior.

13. A body support wrap according to claim 8 wherein said first and second flexible fabric panel surrounding sidewalls are constructed of a combination of nylon and spandex to give an omnidirectional stretch of said first and second flexible fabric panel surrounding sidewalls along said longitudinal, longwise, and lengthwise axes for operationally better encompassing of the body article by said first and second flexible fabric panel surrounding sidewalls in addition to a retaining of the fluid communication element into said open interior.

* * * * *